(12) United States Patent
Panitch et al.

(10) Patent No.: US 9,200,039 B2
(45) Date of Patent: Dec. 1, 2015

(54) EXTRACELLULAR MATRIX-BINDING SYNTHETIC PEPTIDOGLYCANS

(71) Applicant: Symic Biomedical, Inc., San Francisco, CA (US)

(72) Inventors: Alyssa Panitch, West Lafayette, IN (US); John Eric Paderi, West Lafayette, IN (US); Shaili Sharma, West Lafayette, IN (US); Katherine Allison Stuart, West Lafayette, IN (US); Nelda Marie Vazquez-Portalatin, West Lafayette, IN (US)

(73) Assignee: SYMIC IP, LLC, San Francisco, CA (US)

( * ) Notice: Subject to any disclaimer, the term of this patent is extended or adjusted under 35 U.S.C. 154(b) by 0 days.

(21) Appl. No.: 14/214,220

(22) Filed: Mar. 14, 2014

(65) Prior Publication Data

US 2014/0288002 A1    Sep. 25, 2014

Related U.S. Application Data

(60) Provisional application No. 61/798,916, filed on Mar. 15, 2013.

(51) Int. Cl.
| | | |
|---|---|---|
| C07K 14/78 | (2006.01) | |
| A61K 38/39 | (2006.01) | |
| C07K 9/00 | (2006.01) | |
| C07K 14/47 | (2006.01) | |

(52) U.S. Cl.
CPC .............. *C07K 9/00* (2013.01); *C07K 14/4725* (2013.01)

(58) Field of Classification Search
CPC . A61L 2300/236; A61L 24/102; A61L 29/45; A61K 38/39; A61K 81/65; C07K 14/78; C07K 2319/33
See application file for complete search history.

(56) References Cited

U.S. PATENT DOCUMENTS

| | | | |
|---|---|---|---|
| 4,683,298 A | 7/1987 | Yalpani | |
| 5,271,929 A | 12/1993 | Hashiguchi et al. | |
| 5,547,936 A | 8/1996 | Ruoslahti et al. | |
| 5,693,625 A | 12/1997 | Barritault et al. | |
| 5,852,004 A | 12/1998 | Barritault et al. | |
| 5,955,578 A | 9/1999 | Pierschbacher et al. | |
| 5,997,895 A | 12/1999 | Narotam et al. | |
| 6,703,491 B1 | 3/2004 | Homburger et al. | |
| 6,822,071 B1 | 11/2004 | Stephens et al. | |
| 6,864,235 B1 | 3/2005 | Turley et al. | |
| 6,932,973 B2 | 8/2005 | Barritault et al. | |
| 7,098,194 B2 | 8/2006 | Chenite et al. | |
| 7,534,436 B2 | 5/2009 | Courty et al. | |
| 7,592,009 B2 | 9/2009 | Hubbell et al. | |
| 7,671,018 B2 | 3/2010 | Carson et al. | |
| 7,709,439 B2 | 5/2010 | Helmus et al. | |
| 7,732,427 B2 | 6/2010 | Kiick et al. | |
| 7,737,131 B2 | 6/2010 | Kiick et al. | |
| 7,803,905 B2 | 9/2010 | Farach-Carson et al. | |
| 7,842,667 B2 | 11/2010 | Seliktar et al. | |
| 7,851,445 B2 | 12/2010 | Stupp et al. | |
| 7,855,187 B1 | 12/2010 | Prestwich et al. | |
| 7,862,831 B2 | 1/2011 | Wang et al. | |
| 7,897,165 B2 | 3/2011 | Elisseeff et al. | |
| 7,919,111 B2 | 4/2011 | Chudzik et al. | |
| 8,007,774 B2 | 8/2011 | Seliktar et al. | |
| 8,114,834 B2 | 2/2012 | Hsu et al. | |
| 8,188,220 B2 | 5/2012 | Ruoslahti et al. | |
| 8,268,950 B2 | 9/2012 | Elisseeff | |
| 8,283,414 B2 | 10/2012 | Yu et al. | |
| 8,304,388 B2 | 11/2012 | Chettibi et al. | |
| 8,314,195 B2 | 11/2012 | Elisseeff | |
| 8,329,673 B2 | 12/2012 | Prestwich et al. | |
| 8,338,390 B2 | 12/2012 | Kiick et al. | |
| 8,343,764 B2 | 1/2013 | Abad et al. | |
| 8,343,942 B2 | 1/2013 | Oottamasathien et al. | |
| 8,367,639 B2 | 2/2013 | Kilck et al. | |
| 8,389,467 B2 | 3/2013 | Chaput et al. | |
| 8,415,325 B2 | 4/2013 | Kiick et al. | |
| 8,431,146 B2 | 4/2013 | Harley et al. | |
| 8,450,271 B2 | 5/2013 | Shah et al. | |
| 8,470,780 B2 | 6/2013 | Ruoslahti et al. | |
| 8,476,220 B2 | 7/2013 | Barritault et al. | |
| 8,557,774 B2 | 10/2013 | Vandroux et al. | |
| 8,703,740 B2 | 4/2014 | Cho et al. | |
| 8,790,631 B2 | 7/2014 | Barritault et al. | |
| 8,846,003 B2 | 9/2014 | Panitch et al. | |
| 2002/0098153 A1 | 7/2002 | Allen et al. | |
| 2002/0183282 A1 | 12/2002 | Dahricorreia et al. | |
| 2003/0087255 A1 | 5/2003 | Barritault et al. | |
| 2003/0149173 A1 | 8/2003 | Rhee et al. | |
| 2003/0199615 A1 | 10/2003 | Chaput et al. | |

(Continued)

FOREIGN PATENT DOCUMENTS

| | | |
|---|---|---|
| CA | 2299687 | 10/2009 |
| EP | 0462194 | 6/1994 |

(Continued)

OTHER PUBLICATIONS

U.S. Appl. No. 14/119,341, filed Nov. 21, 2013, Panitch et al.
Bernhard, et al. "Synthesis and characterization of an aggrecan mimic," Acta Biomaterialia 8:4 (2012) 1543-1550.
International Search Report and Written Opinion for PCT/US2014/029596, dated Jul. 28, 2014.
Kiani, Chris et al., "Review: Structure and function of aggrecan" Cell Research 12(1), 19-32 (2002).

(Continued)

*Primary Examiner* — Karen Carlson

(74) *Attorney, Agent, or Firm* — Sheppard Mullin Richter & Hampton LLP

(57) ABSTRACT

This disclosure provides extracellular matrix-binding synthetic peptidoglycans comprised of one or more synthetic peptides conjugated to a glycan and methods of their use.

29 Claims, 3 Drawing Sheets

(56) References Cited

U.S. PATENT DOCUMENTS

| | | |
|---|---|---|
| 2004/0091540 A1 | 5/2004 | DesRosiers et al. |
| 2004/0127416 A1 | 7/2004 | Massia et al. |
| 2004/0214272 A1 | 10/2004 | La Rosa et al. |
| 2004/0236092 A1 | 11/2004 | Dziarski et al. |
| 2005/0043221 A1 | 2/2005 | Fallon et al. |
| 2005/0108791 A1 | 5/2005 | Edgerton |
| 2005/0113297 A1 | 5/2005 | Francois et al. |
| 2005/0147679 A1 | 7/2005 | Petito et al. |
| 2005/0187146 A1 | 8/2005 | Helmus et al. |
| 2005/0196377 A1 | 9/2005 | Ratcliffe et al. |
| 2006/0024696 A1 | 2/2006 | Kapur et al. |
| 2006/0075522 A1 | 4/2006 | Cleveland et al. |
| 2006/0123505 A1 | 6/2006 | Kikuchi et al. |
| 2006/0241022 A1 | 10/2006 | Bowen et al. |
| 2006/0252692 A1 | 11/2006 | Lasser et al. |
| 2007/0098675 A1 | 5/2007 | Elisseeff et al. |
| 2007/0124833 A1 | 5/2007 | Abad et al. |
| 2007/0141020 A1 | 6/2007 | Barritault et al. |
| 2007/0167441 A1 | 7/2007 | Halbrook et al. |
| 2007/0218102 A1 | 9/2007 | Chudzik et al. |
| 2007/0224247 A1 | 9/2007 | Chudzik et al. |
| 2007/0298071 A1 | 12/2007 | Harley et al. |
| 2008/0069774 A1 | 3/2008 | Liotta et al. |
| 2008/0090998 A1 | 4/2008 | Abad et al. |
| 2008/0131466 A1 | 6/2008 | Reed et al. |
| 2008/0247995 A1 | 10/2008 | Decarlo et al. |
| 2008/0248569 A1 | 10/2008 | Mata et al. |
| 2009/0022771 A1 | 1/2009 | Lynn et al. |
| 2009/0030525 A1 | 1/2009 | Desrosiers et al. |
| 2009/0075281 A1 | 3/2009 | Hristova et al. |
| 2009/0092674 A1 | 4/2009 | Ingram et al. |
| 2009/0100536 A1 | 4/2009 | Adams et al. |
| 2009/0158452 A1 | 6/2009 | Johnson et al. |
| 2009/0162436 A1 | 6/2009 | Carson et al. |
| 2009/0183270 A1 | 7/2009 | Adams et al. |
| 2009/0202616 A1 | 8/2009 | Chong et al. |
| 2009/0324722 A1 | 12/2009 | Elisseeff et al. |
| 2010/0003329 A1 | 1/2010 | Elisseeff et al. |
| 2010/0004196 A1 | 1/2010 | De Agostini et al. |
| 2010/0017904 A1 | 1/2010 | Abad et al. |
| 2010/0021545 A1 | 1/2010 | Chaput et al. |
| 2010/0029549 A1 | 2/2010 | Chaput et al. |
| 2010/0111842 A1 | 5/2010 | Boyden et al. |
| 2010/0119577 A1 | 5/2010 | Min et al. |
| 2010/0137510 A1 | 6/2010 | Seliktar et al. |
| 2010/0166830 A1 | 7/2010 | Harley et al. |
| 2010/0210509 A1 | 8/2010 | Oh et al. |
| 2010/0227836 A1 | 9/2010 | Elisseeff et al. |
| 2011/0020298 A1 | 1/2011 | Panitch et al. |
| 2011/0038828 A1 | 2/2011 | Seliktar et al. |
| 2011/0087152 A1 | 4/2011 | David et al. |
| 2011/0207669 A1 | 8/2011 | Vandroux et al. |
| 2011/0214206 A1 | 9/2011 | La Rosa et al. |
| 2011/0238000 A1 | 9/2011 | Seliktar et al. |
| 2011/0258734 A1 | 10/2011 | Adams et al. |
| 2011/0269208 A1 | 11/2011 | Burdick et al. |
| 2012/0020911 A1 | 1/2012 | Seliktar et al. |
| 2012/0034164 A1 | 2/2012 | Ruoslahti et al. |
| 2012/0058943 A1 | 3/2012 | Werner et al. |
| 2012/0100106 A1 | 4/2012 | Panitch et al. |
| 2012/0227131 A1 | 9/2012 | Abad et al. |
| 2012/0246748 A1 | 9/2012 | Guo et al. |
| 2012/0258068 A1 | 10/2012 | Seliktar et al. |
| 2012/0294925 A1 | 11/2012 | Lynn et al. |
| 2013/0035307 A1 | 2/2013 | Prestwich et al. |
| 2013/0045926 A1 | 2/2013 | DeVore et al. |
| 2013/0052155 A1 | 2/2013 | Marcolongo et al. |
| 2013/0074202 A1 | 3/2013 | Adams et al. |
| 2013/0101628 A1 | 4/2013 | Webber et al. |
| 2013/0109808 A1 | 5/2013 | Elisseeff |
| 2013/0116405 A1 | 5/2013 | Yu et al. |
| 2013/0152224 A1 | 6/2013 | Abad et al. |
| 2013/0190246 A1 | 7/2013 | Paderi et al. |
| 2013/0196896 A1 | 8/2013 | Komatsu et al. |
| 2013/0323311 A1 | 12/2013 | Paderi et al. |
| 2013/0333061 A1 | 12/2013 | Wu et al. |
| 2014/0288002 A1 | 9/2014 | Panitch et al. |
| 2014/0301972 A1 | 10/2014 | Barritault et al. |
| 2014/0301983 A1 | 10/2014 | Panitch et al. |

FOREIGN PATENT DOCUMENTS

| | | |
|---|---|---|
| EP | 1586652 | 10/2005 |
| EP | 1677807 | 9/2010 |
| EP | 2292773 | 3/2011 |
| EP | 2295582 | 3/2011 |
| JP | 2000-109500 | 4/2000 |
| JP | 2005185101 | 7/2005 |
| WO | WO-92/12175 | 7/1992 |
| WO | WO 9927105 | 6/1999 |
| WO | WO-01/19386 | 3/2001 |
| WO | WO-2005/055800 | 6/2005 |
| WO | WO-2005/061018 | 7/2005 |
| WO | WO-2005/082430 | 9/2005 |
| WO | WO-2005/116066 | 12/2005 |
| WO | WO-2006/047758 | 5/2006 |
| WO | WO-2006/130974 | 12/2006 |
| WO | WO 2007/044026 | 4/2007 |
| WO | WO 2008034648 | 3/2008 |
| WO | WO 2008/066816 | 6/2008 |
| WO | WO 2008070179 | 6/2008 |
| WO | WO-2008/126092 | 10/2008 |
| WO | WO-2008/152639 | 12/2008 |
| WO | WO 2009-120995 | 10/2009 |
| WO | WO 2009120995 | 10/2009 |
| WO | WO 2010033564 | 3/2010 |
| WO | WO-2010/122232 | 10/2010 |
| WO | WO 2010115156 | 10/2010 |
| WO | WO-2010/139953 | 12/2010 |
| WO | WO-2011/057286 | 5/2011 |
| WO | WO-2011/094149 | 8/2011 |
| WO | WO-2011/156445 | 12/2011 |
| WO | WO 2011163492 | 12/2011 |
| WO | WO 2012-112767 | 8/2012 |
| WO | WO 2012/0162534 | 11/2012 |
| WO | WO-2013/110056 | 7/2013 |
| WO | WO-2014/028209 | 2/2014 |
| WO | WO-2014/038866 | 3/2014 |
| WO | WO-2014/040591 | 3/2014 |
| WO | WO-2014/071132 | 5/2014 |
| WO | WO 2014099997 | 6/2014 |

OTHER PUBLICATIONS

Lee, H. J. et al. "Enhanced chondrogenesis of mesenchymal stem cells in collagen mimetic peptidemediated microenvironment" Tissue Engineering Part A, 14(11) 1843-51 (2008).

Ogden, David A., "Clinical responses to new and reprocessed hemodialyzers." Guide to Reprocessing of Hemodialyzers 87-97 (1986).

Paderi, "Design of collagen binding proteoglycan mimics." Thesis (Aug. 2008).

Paderi, John E., et al., "The Inhibition of Platelet Adhesion and Activation on Collagen During Balloon Angioplasty by Collagen-Binding Peptidoglycans" Biomaterials, 32, 2516-2523 (2011).

Pierce Biotechnology catalog (2005/2006).

Roth, Gerald J. et al; "Localization of binding sites within human von willebrand factor for monomeric type III collagen." Biochemistry 25, 8357-8361 (1986).

Santa Cruz Biotechnology listing for phosphate buffered saline (http://www.scbt.com/datasheet-362182.html, downloaded Feb. 10, 2014).

Saxena, Anil K. et al; "Enhancing the survival of tunneled haemodialysis catheters using an antibiotic lock in the elderly: a randomized, double blind clinical trial." Nephrology 11, 299-305 (2006).

Hemmer, et al. (2000) "Minimal peptide length requirements for CD4+T cell clones—implications for molecular mimicry and T cell survival" Intl. Immunol., 12(3) 375-383.

Julienne, et al., (2014), "Topical treatment with a new matrix therapy agent (RGTA, CACICOL-20) improves epithelial wound healing after penetrating keratoplasty," Acta Ophthalmologica, 92(s253), 3 pages.

(56) References Cited

OTHER PUBLICATIONS

Kirker, et al., (2002), "Glycosaminoglycan hydrogel films as biointeractive dressings for wound healing," Biomaterials, 23(17):3661-3671.
Larroque, et al. (2013), "New matrix therapy in chronic corneal ulcers resistant to conventional therapies," Acta Ophthalmologica, 91(s252), 2 pages.
Lynn, et al., (2010), "Design of a multiphase osteochondral scaffold. I. Control of chemical composition," J Biomed Mater Res A, 92(3):1057-1065.
O'Brien, et al., (2005), "The effect of pore size on cell adhesion in collagen-GAG scaffolds," Biomaterials, 26(4):433-441.
Place, et al., (2014), "Aggrecan-mimetic, glycosaminoglycan-containing nanoparticles for growth factor stabilization and delivery," Biomacromolecules, 15(2):680-689.
Place, et al., (2014), "Synthesis and characterization of proteoglycan-mimetic graft copolymers with tunable glycosaminoglycan density," Biomacromolecules, 15(10):3772-3780.
Van Neck, et al., (Mar. 30, 2012), "Heparan Sulfate Proteoglycan Mimetics Promote Tissue Regeneration: An Overview," Chapter 4 in J Davies (Ed.), Tissue Regeneration—From Basic Biology to Clinical Application, 69-92, InTech—Open Access Publisher, ISBN 978-953-51-0387-5, 520 pages.
Zhang, et al. (2014), "Preservation of the structure of enzymatically-degraded bovine vitreous using synthetic proteoglycan mimics," Invest Ophthalmol Vis Sci, 55: 8153-8162. doi:10.1167/ iovs.14-14366.
U.S. Appl. No. 14/474,832, filed Sep. 2, 2014, John E. Paderi et al.
U.S. Appl. No. 14/466,889, filed Aug. 22, 2014, Alyssa Panitch et al.
U.S. Appl. No. 14/497,189, filed Sep. 25, 2014, Alyssa Panitch et al.
Adiguzel, et al., "Collagens in the progression and complications of atherosclerosis" Vascular Medicine. 14, 73-89. (2009).
Allaire, et al., "Endothelial Cell Injury in Cardiovascular Surgery: The Intimal Hyperplastic Response" Ann Thorac Surg, 63(2), 582-91, (1997).
Ando, "Opinion Statement of the Effect of Mechanical Stress on Carilage Tissue Engineering" The Open Bone Journal, 2, 32-37 (2010).
Armstrong, David G. et al., "The Role of Matrix Metalloproteinases in Wound Healing" J Am Podiatr Med Assoc, 92(1), 12-18 (2002).
Ashcroft et al.; "Aging alters the inflammatory and endothelial cell adhesion molecule profiles during human cutaneous wound healing" Laboratory Investigation 78(1), 47-58, (1998).
Bernhard et al,. "Synthesis and characterization of an aggrecan mimic" Acta Biomaterialia 8(4),1543-1550, (2012).
Bhide et al., "Collagen Phagocytosis by Fibroblasts Is Regulated by Decorin" J. Biol. Chem., 280(24), 23103-23113 (2005).
Bierbaum et al., "Collageneous Matrix Coatings on Titanium Implants Modified with Decorin and Chondroitin Sulfate: Characterization and Influence on Osteoblastic Cells" Journal of Biomedical Materials Research, 77A, 551-562. (2006).
Birch, Mary et al., "Animal Models for Adult Dermal Wound Healing" Methods in Molecular Medicine, 117, 223-235 (2005).
Braunwald et al., "The Problem of Persistent Platelet Activation in Acute Coronary Syndromes and Following Percutaneous Coronary Intervention" Clinical Cardiology. 31(3 Suppl. 1), I17-I20.( 2008).
Brem, Harold et al., "Cellular and molecular basis of wound healing in diabetes," The Journal of Clinical Investigation, 117(5), 1219-22 (2007).
Broughton et al; "The basic science of wound healing." Plastic and Reconstructive Surgery 117(7S), 12S-34S (2006).
Business Wire "ZymoGenetics Reports New Findings on Anti-thrombotic Activities of CTRP1; Novel Protein Prevents Platelet Thrombosis without Causing Bleeding", www.thefreelibrary.com/ZymoGenetics+Reports+New+Findings+on+Anti-thrombotic+Activities+of+a0105542135, pp. 1-3 (2003).
Chiang et al., "Cloning, Characterization, and Functional Studies of a 47-kDa Platelet Receptor for Type III Collagen" The Journal of Biological Chemistry, 277( 38), 34896-34901 (2002).

Chiang et al., "Peptides Derived From Platelet Non-Integrin Collagen-Receptors or Types I and III Collagen Inhibit Collagen-Platelet Interaction" Cardiovascular & Haematological Disorders-Drug Targets, 7(1), 71-75 (2007).
Chiang, Thomas M., et al., "A Synthetic Peptide Derived from the Sequence of a Type I Collagen Receptor Inhibits Type I Collagen-Mediated Platelet Aggregation" The Journal of Clinical Investigation, 100(8), 2079-2084 (1997).
Chung C. et al., "Influence of gel properties on neocatilage formation by auricular chondrocytes photoencapsulated in hyaluronic acid networks" Journal of Biomedical Materials Research Part A, 77(3), 518-25 (2006).
Chung, C. et al. "The influence of degradation characteristics of hyaluronic acid hydrogels on in vitro neocartilage formation by mesenchymal stem cells" Biomaterials, 30(26), 4287-96 (2009).
Chupa, Janeen M., et al., "Vascular Cell Responses to Polysaccharide Materials: In Vitro and In Vivo Evaluations" Biomaterials, 21, 2315-2322 (2000).
Danielson, Keith G. et al., "Targeted Disruption of Decorin Leads to Abnormal Collagen Fibril Morphology and Skin Fragility" The Journal of Cell Biology, 136, 729-743 (1997).
Demling, Robert H. et al., "Small Intestinal Submucosa Wound Matrix and Full-thickness Venous Ulcers: Preliminary Results" Wounds Research, 16(1), 18-22 (2004).
Di Mario, et al. "The "Dark Side" of Percutaneous Coronary Interventions" Journal of the American College of Cardiology Interventions, 1(3):277-278 (2008).
Drachman, et al., "Inflammation as a Mechanism and Therapeutic Target for In-stent Restenosis" Current Atherosclerosis Reports; 7(1), 44-49 (2005).
Extended European Search Report for EP11798931, completed Dec. 4, 2013.
Falanga, Vincent "Wound healing and its impairment in the diabetic foot," Lancet, 366, 1736-43 (2005).
Farb, et al. "Pathology of Acute and Chronic Coronary Stenting in Humans" Circulation, 99, 44-52 (1999).
FDA, "Guidance for Industry Chronic Cutaneous Ulcer and Burn Wounds Developing Products for Treatment" (Jun. 2006).
Flaumenhaft, Robert et al., "Extracellular Matrix Regulation of Growth Factor and Protease Activity" 1991, Current Opinion in Cell Biology, 3, 817-23 (1991).
Fransson, Lars-Åke et al., "Periodate Oxidation and Alkaline Degradation of Heparin-Related Glycans" Carbohydrate Research, 80, 131-145 (1980).
Fulzele, et al., "Study of the Biodegradation and In Vivo Biocompatibility of Novel Biomaterials" European Journal of Pharmaceutical Sciences, 20, 53-61(2003).V.
Gallant-Behm, Corrie L. et al., "Cytokine and Growth Factor mRNA Expression Patterns Associated with the Hypercontracted, Hyperpigmented Healing Phenotype of Red Duroc Pigs: A Model of Abnormal Human Scar Development?" J Cutan Med Surg, 9(4), 165-177 (2005).
Gallant, Corrie L. et al., "Molecular, histologic, and gross phenotype of skin wound healing in red Duroc pigs reveals an abnormal healing phenotype of hypercontracted, hyperpigmented scarring" Wound Rep Reg, 12, 305-319 (2004).
Geng, Yeqing et al., "SLRP interaction can protect collagen fibrils from cleavage by collagenases" Matrix Biology, 25, 484-491 (2006).
Gercken, et al. "Results of the Jostent Coronary Stent Graft Implantation in Various Clinical Settings: Procedural and Follow-Up Results" Catheterization and Cardiovascular Interventions.; 56 (3), 353-360 (2002).
Goldoni, Silvia et al; "Biologically active decorin is a monomer in solution." J. Bio. Chem. 279(8), 6606-6612 (2004).
Grassl, E. D., et al., "Fibrin as an Alternative Biopolymer to Type-1 Collagen for the Fabrication of a Media Equivalent" Journal of Biomedical Materials Research, 60(4), 607-612, (2002).
Griese, Daniel P., et al., "Isolation and Transplantation of Autologous Circulating Endothelial Cells Into Denuded Vessels and Prosthetic Grafts: Implications for Cell-Based Vascular Therapy" Circulation, 108, 2710-2715 (2003).
Griffey, et al., "Particulate Dermal Matrix as an Injectable Soft Tissue Replacement Material" J. Biomed. Mater. Res., 58, 10-15 (2001).

(56) References Cited

OTHER PUBLICATIONS

Gutman, et al., "Liposomal alendronate for the treatment of restenosis" Journal of Controlled Release, 161, 619-627 (2012).
Hantgan, et al; "Platelets interact with fibrin only after activation." Blood, 65(6) 1299-1311 (1985).
Helms, Brett A. et al. "High affinity peptide based collagen targeting using synthetic phage mimics: from phage display to dendrimerdisplay." J. Am. Chem. Soc.131, 11683-11685 (2009).
Henn, et al; "CD40 ligand on activated platelets triggers an inflammatory reaction of endothelial cells." Nature, 391, 591-594 (1998).
Hermanson, "Zero-Length Cross-Linkers" Academic Press, 169-186 (1996).
Huizinga et al., "Crystal Structure of the A3 Domain of Human Von Willebrand Factor: Implications for Collagen Binding" Structure, 5 (9), 1147-1156 (1997).
Hunt et al., "Respiratory Gas Tensions and pH in Healing Wounds" American Journal of Surgery, 114, 302-307, (1967).
International Search Report/Written Opinion for PCT/US2009/038624 mailed Sep. 28, 2010.
International Search Report/Written Opinion for PCT/US2010/033543 issued Oct. 8, 2010.
International Preliminary Examination Report along with Written Opinion of the International Searching Authority issued in International PCT application No. PCT/US2012/039404 issued Apr. 17, 2013.
International Preliminary Examination Report issued in International PCT application No. PCT/US2009/038624 mailed Dec. 7, 2009.
International Search Report issued in International Application No. PCT/US2012/039404 mailed Apr. 29, 2013.
Järveläinen, Hannu et al., "A role for decorin in cutaneous wound healing and angiogenesis" Wound Rep Reg, 14, 443-452 (2006).
Järvinen, Tero A. H. et al., "Target-seeking antifibrotic compound enhances wound healing and suppresses scar formation in mice" PNAS, 107(50), 21671-21676 (2010).
Kalamajski et al., "The Decorin Sequence SYIRIADTNIT Binds Collagen Type 1" Journal of Biological Chemistry, 282(22), 16062-16067 (2007).
Kalamajski, "The role of small leucine-rich proteoglycans in collagen fibrillogenesis" Matrix Biology, 29(4), 248-253 (2010).
Khorramizadeh, M.R. et al., "Aging differentially modulates the expression of collagen and collagenase in dermal fibroblasts" Molecular and Cellular Biochemistry, 194, 99-108 (1999).
Kipshidze et al., "Role of the Endothelium in Modulating Neointimal Formation" Journal of the American College of Cardiology, 44(4), 733-739 (2004).
Kitov, Pavel I. and Bundle, David R., "On the nature of the multivalency effect: a thermodynamic model." J. Am. Chem. Soc., 125, 16271-16284 (2003).
Kraut et al; "Challenges in enzyme mechanism and energetics." Annu. Rev. Biochem., 72, 517-571 (2003).
Lasser, Blood, 2006, 107, 423-430.
Lazic, Tamara et al., "Bioengineered Skin Constructs and Their Use in Wound Healing" 2010, Plastic and Reconstructive Surgery, 127(1S), 75S-90S (2010).
Lemon, Stanley M. et al; "Immunoprecipitation and virus neutralization assays demonstrate qualitative differences between protective antibody responses to inactivated hepatitis a vaccine and passive immunization with immune globulin." J. Infect. Disease 179, 9-19 (1997).
Libby et al. "A Cascade Model for Restenosis—A Special Case of Atherosclerosis Progression" Circulation., 86(6), III-47-III-52 (1992).
Mammen, Mathai, et al., "Polyvalent Intercactions in Biological Systems: Implications for Design and Use of Multivalent Ligands and Inhibitors" Angew. Chem. Int. Ed., 37, 2754-2794 (1998).
Martin, Paul "Wound Healing—Aiming for Perfect Skin Regeneration" Science, 276, 75-81, (1997).
Moustafa, M. et al., "A new autologous keratinocyte dressing treatment for non-healing diabetic neuropathic foot ulcers" Diabetic Medicine, 21, 786-789 (2004).
Mummert, "Immunological Roles of Hyaluronan" Immunologic Research, 31(3), 189-205 (2005).
Nili, Nafiseh et al., "Decorin inhibition of PDGF-stimulated vascular smooth muscle cell function: potential mechanism for inhibition of intimal hyperplasia after balloon angioplasty" The American Journal of Pathology, 163(3), 869-878 (2003).
Orbusneich, "About the Combo Dual Therapy Stent.".
Oyama et al; "Isolation of lung tumor specific peptides from a random peptide library: generation of diagnostic and cell targeting reagents." Cancer Letters, 202, 219-230 (2003).
Paderi et al., "Design of a Synthetic Collagen-Binding Peptidoglycan that Modulates Collagen Fibrillogenesis" Biomacromolecules, 9, 2562-2566 (2008).
Paderi, John E. et al., "Collagen-Binding Peptidoglycans: A Biomimetic Approach to Modulate Collagen Fibrillogenesis for Tissue Engineering Applications" Tissue Engineering: Part A, 15(10), 2991-2999 (2009).
PCT Search Report and Written Opinion for PCT/US2011/041654, mailed Nov. 7, 2011.
Penc, Stanley F. et al., "Dermatan Sulfate Released after Injury is a Potent Promoter of Fibroblast Growth Factor-2 Function" The Journal of Biological Chemistry, 273(43), 28116-28121 (1998).
Pentikainen, Markku O. et al; "The proteoglycan decorin links low density lipoproteins with collagen type I." J. Bio. Chem. 272(12), 7633-7638 (1997).
Pieper, J.S., et al., "Development of Tailor-Made Collagen-GLycosaminoglycan Matrices: EDC/NHS Crosslinking, and Ultrastructural Aspects" Biomaterials, 21, 581-593 (2000).
Pignatelli et al; "Hydrogen preoxide is involved in collagen induced platelet activation" Blood, 91(2) 484-490 (1998).
Pizzo et al., "Extracellular Matrix (ECM) Microstructural Composition Regulates Local Cell-ECM Biomechanics and Fundamental Fibroblast Behavior: A Multidimensional Perspective" Journal Appl. Physiol, 98, 1909-1921 (2005).
Puig, A. et al., "A new decorin-like tetrapeptide for optimal organization of collagen fibres" International Journal of Cosmetic Science, 30, 97-104 (2008).
Radek, Katherine A. et al., "FGF-10 and specific structural elements of dermatan sulfate size and sulfation promote maximal keratinocyte migration and cellular proliferation" Wound Rep Reg, 17, 118-126 (2009).
Ratcliffe, Anthony, "Tissue Engineering of Vascular Grafts" Matrix Biology, 19, 353-357 (2000).
Reed, Charles C. et al., "The role of decorin in collagen fibrillogenesis and skin homeostasis" Glycoconjugate Journal, 19, 249-255 (2003).
Roeder et al., "Tensile Mechanical Properties of Three-Dimensional Type I Collagen Extracellular Matrices With Varied Microstructure" Transactions of the ASME, 124, 214-222 (2002).
Romijn et al., "Mapping the Collagen-Binding Site in the Von Willebrand Factor-A3 Domain" The Journal of Biological Chemistry, 278(17), 15035-15039 (2003).
Roseborough et al; "Prevention and treatment of excessive dermal scarring." J. Natl. Med. Assoc., 96,108-116 (2004).
Rosenblum et al., "Diminished Benefits of Drug-Eluting Stents versus Bare Metal Stents in Patients with Severe Renal Insufficiency" Nephron Clinical Practice, 113, c198-c202, (2009).
Rossi, Francois et al; "Decontamination of surfaces by low pressure plasma discharges" Plasma Process. Polym. 3, 431-442 (2006).
Roy-Chaudhury et al. "Hemodialysis Vascular Access Dysfunction: A Cellular and Molecular Viewpoint" J Am Sco Nephrol, 17(4),1112-1127 (2006).
Rudbach, J. A. et al; "Physical aspects of reversible inactivation of endotoxin." Ann. New York Acad. Sci., 133, 629-643 (1966).
Schilling et al., "Wound Healing: A Comparative Study of the Histochemical Changes in Granulation Tissue Contained in Stainless Steel Wire Mesh and Polyvinyl Sponge Cylinders" Surgery, 46(4), 702-710 1959.
Schonherr et al., "Decorin Core Protein Fragment LEU 155-Val260 Interacts with TGF-Beta But Does Not Compete for Decorin Binding to Type I Collagen" Arch. Biochem. Biophys., 355(2), 241-248 (1998). Abstract Only.

(56) References Cited

OTHER PUBLICATIONS

Schultz, Gregory S. et al., "Interactions between extracellular matrix and growth factors in wound healing" Wound Rep Reg, 17, 153-62 (2009).
Scott et al., "Chemical characterization and quantification of proteoglycans in human post-burn hypertrophic and mature scars" Clinical Science, 90(5), 417-25 (1996).
Scott, et al., "Decorin mimic inhibits vascular smooth muscle proliferation and migration" PLOS One, 8(11 ): e82456. (2013).
Scott, John E. et al., "Dermatan sulphate-rich proteoglycan associates with rat tail-tendon collagen at the d band in the gap region" Biochem. J., 197(1), 213-216 (1981).
Scott, John E. et al., "Proteoglycan-fibrillar collagen interactions" Biochem. J, 252, 313-323 (1988).
Scott, Paul G. et al., "Molecular and Cellular Aspects of Fibrosis Following Thermal Injury" Thermal Injuries, 16(2), 271-287 (2000).
Shin, Min Kyoung et al, "A novel collagen-binding peptide promotes osteogenic differentiation via $Ca^{2+}$/calmodulin-dependent protein kinase II/ERK/AP-1 signaling pathway in human bone marrow-derived mesenchymal stem cells", Cellular Signaling, 20, 613-624 (2008).
Singer, Adam et al., "Cutaneous Wound Healing" The New England Journal of Medicine, 341(10), 738-46 (1999).
Sini et al; "Role of decorin on in vitro fibrillogenesis of type 1 collagen."Glycoconj. J. 14, 871 -874 (1997).
Stuart, et al., "Collagen-Binding peptidoglycans inhibit MMP mediated collagen degradation and reduce dermal scarring" PLOS One, 6(7), e22139 2011.
Suki, Bela et al., "Biomechanis of the lung parenchyma: critical roles of collagen and mechanical forces" J. Appl. Physiol. 98, 1892-1899 (2005).
Svensson et al., "Decorin-binding sites for collagen type I are mainly located in leucine-rich repeats 4-5" J. Biol. Chem., 270(35), 20712-20716 (1995).
Taylor, Kristen R. et al., "Structural and Sequence Motifs in Dermatan Sulfate for Promoting Fibroblast Growth Factor-2 (FGF-2) and FGF-7 Activity" The Journal of Biological Chemistry, 280(7), 5300-5306 (2005).
Tenni et al., "Interaction of Decorin with CNBr Peptides from Collagens I and II Evidence for Multiple Binding Sites and Essential Lysyl Residues in Collagen" Eur. J. Biochem., 269, 1428-1437 (2002).
The USRDS Coordinating, "Incidence, prevalence, patient characteristics, and treatment modality" Center United States Renal Data System, 2, 215-228 (2013).
Tollefsen, "Vascular Dermatan Sulfate and Heparin Cofactor II" Progress in Molecular Biology and Translational Science, 93, 351-372 (2010).
Trengove, Naomi J. et al., "Analysis of the acute and chronic wound environments: the role of proteases and their inhibitors" Wound Rep Reg, 7(6), 442-452 (1999).
Trowbridge, Janet M. et al., "Derman sulfate: new functions from an old glycosaminoglycan" Glycobiology, 12(9), 117R-125R (2002).
Trowbridge, Janet M. et al., "Dermatan Sulfate Binds and Potentiates Activity of Keratinocyte Growth Factor (FGF-7)" The Journal of Biological Chemistry, 277(45), 42815-42820 (2002).
U.S. Appl. No. 13/318,710 Final Rejection dated Mar. 27, 2014.
U.S. Appl. No. 13/318,710 Non-Final Rejection dated Aug. 21, 2013.
U.S. Appl. No. 12/934,551 Non-Final Rejection dated Jun. 6, 2013.
U.S. Appl. No. 12/934,551 Final Rejection dated Jan. 17, 2014.
U.S. Appl. No. 13/806,438 Non-Final Rejection dated Mar. 3, 2014.
Uniprot/Trembl Q7Z4J1, "Nonintegrin Platelet Receptor for Type I Collagen", Last Modified Feb. 10, 2009, Available on the Internet <URL: http://www.uniprot.org/uniprot/Q7Z4J1 &format=html.
Uniprotkb, "Decorin Precursor—Bas Taurus (Bovine)", Last Modified Sep. 1, 2009, Available on the Internet <URL: http://www. un iprotorg/uniprot/P21793>.
Velander, Patrik et al., "Impaired wound healing in an acute diabetic pig model and the effects of local hyperglycemia" Wound Rep Reg, 16, 288-93 (1999).

Vogel, Kathryn G. et al., "Specific. inhibition of type I and type II collagen fibrillogenesis by the small proteoglycan of tendon" Biochem J, 223, 587-597 (1984).
Wang, et al., "Venous stenosis in a pig arteriovenous fistula model—anatomy, mechanisms and cellular phenotypes" Nephrol Dial Transplace, 23:525-533 (2008).
Wang, JianFei et al., "Deep dermal fibroblasts contribute to hypertrophic scarring" Laboratory Investigation, 88, 1278-1290 (2008).
Wang, Kai, et al., "Platelet, Not Endothelial, P-Selectin Is Required for Neointimal Formation After Vascular Injury", Arterioscler Thromb. Vase. Biol., No. 25, pp: 1584-1589 (2005).
Widgerow, Alan D. et al., "Multimodality Scar Management Program" Aesth Plast Surg, 33, 533-543 (2009).
Williams, et al; "Collagen fibril formation." J. Biol. Chem., 253(18), 6578-6585 (1978).
Wysocki, Annette B. et al., "Wound Fluid from Chronic Leg Ulcers Contains Elevated Levels of Metalloproteinases MMP-2 and MMP-9" The Society for Investigative Dematology, Inc., 101(1), 64-68 (1993).
Zhu, Kathy Q. et al, "Further similarities between cutaneous scarring in the female, red Duroc pig and human hypertrophic scarring" Burns, 30, 518-530 (2004).
Zhu, Kathy Q. et al., "Review of the female Duroc/Yorkshire pig model of human fibroproliferative scarring" Wound Rep. Reg., 15, S32-S39 (2007).
Zhu, Kathy Q. et al., "The female, red Duroc pig as an animal model of hypertrophic scarring and the potential role of the cones of skin" Burns, 29, 649-664 (2003).
Zustiak, S. P. et al. Influence of cell-adhesive peptide ligands on poly(ethylene glycol) hydrogel physical, mechanical and transport properties. Acta Biomaterialia, 6(9), 3404-14 (2010).
Basser, Peter J. et al., "Mechanical Properties of the Collagen Network in Human Articular Cartilage as Measured by Osmotic Stress Technique" Archives of Biochemistry and Biophysics, 351(2), 207-219 (1998).
Maroudas, A, "Balance between Swelling pressure and collagen tension in normal and degenerate cartilage" Nature, 260, 808-809 (1976).
Christner, J.E. "Studies on the properties of the inextricable proteoglycans from bovine nasal cartilage" J. Biol. Chem. 258, 14335-14341 (1983).
Hollander, Anthony P. et al., "Increased Damage to Type II Collagen in Osteoarthritic Articular Cartilage Detected by a New Immunassay" J. Clin. Invest., 93, 1722-1732 (1994).
Knudson, Cheryl B. et al., "Cartilage Proteoglycans" Cell & Developmental Biology, 12, 69-78 (2001).
Pratta, Michael A. et al., "Glycobiology and Extracellular Matrices: Aggrecan Protects Cartilage Collagens from Proteolytic Cleavage" J. Biol. Chem., 278(46), 45539-45545 (2003).
Madsen, Suzi Hoegh et al., "Aggrecanase- and matrix metalloproteinase-mediated aggrecan degradation is associated with different molecular characteristics of aggrecan and separated in time ex vivo" Biomarkers, 15(3) 266-276 (2010).
Sharma, Shaili et al., "Biomimetic Aggrecan Reduces Cartilage Extracellular Matrix From Degradation and Lowers Catabolic Activity in Ex Vivo and In Vivo Modelsa" Macromolecular Bioscience, DOI 10.1002, 1-10 (2013).
Schmitz, Ian et al., "Hyaluronan oligosaccharide treatment of chondrocytes stimulates expression of both HAS-2 and MMP-3, but by different signaling pathways" Osteoarthritis Cartilage, 18(3), 447-454 (2010).
Klatt, Andreas R. et al., "A Critical Role for Collagen II in Cartilage Matrix Degradation: Collagen II Induces Pro-Inflammatory Cytokines and MMPs in Primary Human Chondrocytes" J. Orthop Res (27) 65-70 (2009).
Kapoor, Mohit et al., "role of proinflammatory cytokines in the pathophysiology of osteoarthritis" Nat. Rev. Rheumatol, 7, 33-42 (2011).
Lee, Seulki et al., "Dark Quenched Matrix Metalloproteinase Fluorogenic Probe for Imaging Osteoarthritis Development in Vivo" Bioconjugate Chemistry, 19(9), 1743-1747 (2008).

(56) References Cited

OTHER PUBLICATIONS

Lee, Seulki et al., "Polymeric Nanoparticle-Based Activatable Near-Infrared Nanosensor for Protease Determination In Vivo" Nano Lett., 9(12), 4412-4416 (2009).
Gerwin, Nicole "Intraarticular drug delivery in osteoarthritis" Advanced Drug Delivery Reviews, 58, 226-242 (2006).
Rutjes, Anne et al., "Viscosupplementation for Osteoarthritis of the Knee: A Systematic Review and Meta-analysis" Ann Intern Med., (157), 180-191 (2012).
Masuko, Kayo et al., "Anti-inflammatory effects of hyaluronan in arthritis therapy: Not just for viscosity" International Journal of General Medicine, 2, 77-81 (2009).
Ghosh, Peter et al., "The Effects of Intraarticular Administration of Hyaluronan in a Model of Early Osteoarthritis in Sheep I. Gait Analysis and Radiological and Morphological Studies" Seminarsin Arthritisand Rheumatism, 22(6), 18-30 (1993).
Smith Jr., Gerald N. et al., "Effect of Intraarticular Hyaluronan Injection in Experimental Canine Osteoarthritis" Arthritis & Rheumatism, 41(6), 976-985 (1998).
Fraser, J. R. E. et al., "Hyaluronan: its nature, distribution, functions and turnover" Journal of Internal Medicine, 242, 27-33 (1997).
Kraus, Virgina B. et al., "The OARSI Histopathology Initiative—Recommendations for Histological Assessments of Osteoarthritis in the Guinea Pig" Osteoarthritis Cartilage, 18(Suppl. 3), S35-S52 (2010).
A National Public Health Agenda for Osteoarthritis 2010, www.cdc.gov/arthritis/docs/OAagenda.pdf (2010).
Madry, Henning et al., "Biological aspects of early osteoarthritis" Knee Surg Sports Traumator Arthrosc, 20, 407-422 (2012).
Pratta, Michael A. et al., "Aggrecan Protects Cartilage Collagen from Proteolytic Cleavage" J. Biol. Chem., 278(46), 45539-45545 (2003).
Huang, K. et al., "Aggrecanase and Aggrecan Degradation in Osteoarthritis: a Review" The Journal of International Medical Research, 36, 1149-1160 (2008).
Nagase, Hideaki et al., "Review: Aggrecanases and cartilage matrix degradation" Arthritis Research & Therapy, 5(2), 94-103 (2003).
Umlauf, Daniel et al., "Cartilage biology, pathology, and repair" Cell. Mol. Life Sci., 67, 4197-4211 (2010).
Nia, Hadi Tavakoli et al., "High-Bandwidth AFM-Based Rheology Reveals that Cartilage is Most Sensitive to High Loading Rates at Early Stages of Impairment" Biophysical Journal, 104, 1529-1537 (2013).
Lee, Young Ho et al., "Effect of glucosamine or chondroitin sulfate on the osteoarthritis progression: a meta-analysis" Rheumatol Int., 30, 357-363 (2010).
Henrotin, Yves et al., "Intra-articular use of a medical device composed of hyaluronic acid and chondroitin sulfate (Structovial CS): effects on clinical, ultrasonographic and biological parameters" BMC Research Notes, 5(407), 1-7 (2012).
Mummert, Mark E. et al., "Development of a Peptide Inhibitor of Hyaluronan-mediated Leukocyte Trafficking" J. Exp. Med., 192(6), 769-779 (2000).
Martel-Pelletier, Johanne et al., "Review: Future therapeutics for osteoarthritis" Bone, 51, 297-311 (2012).
Kiani, Chris et al., "Review: Structure and function of aggrecan" Cell Research, 12(1), 19-32 (2002).
Carney, S.L. et al., "The Structure and Function of Cartilage Proteoglycans" Physiological Reviews, 68(3), 858-910 (1988).
Cremer, Michael A. et al., "The cartilage collagens: a review of their structure, organization, and role in the pathogenesis of experimental arthritis in animals and in human rheumatic disease" J Mol Med, 76, 275-288 (1998).

EXTRACELLULAR MATRIX-BINDING SYNTHETIC PEPTIDOGLYCANS

CROSS-REFERENCE TO RELATED APPLICATION

This application claims the benefit under 35 U.S.C. §119 (e) of U.S. Provisional Application Ser. No. 61/798,916, filed Mar. 15, 2013, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 10, 2014, is named 39WG-197593-US_SL.txt and is 22,178 bytes in size.

FIELD OF INVENTION

This disclosure provides extracellular matrix-binding synthetic peptidoglycans comprised of one or more synthetic peptides conjugated to a glycan and methods of their use.

BACKGROUND

In most tissues, cells are surrounded by an extracellular matrix (ECM) containing proteins such as collagen, laminin, and fibronectin. As mammals age and in some disease states, the extracellular matrix in certain areas of the body (e.g., in synovial joints, the vitreous humor, the spinal discs, the skin, etc.) can degrade, causing undesirable symptoms, such as various forms of arthritis, loss of vision, and the like.

Lubricin, also known as superficial zone protein (SZP) or PRG4, is a mucinous glycoprotein secreted by tissues lining the interior surfaces of animal joints (see Schumacher, B. L., et al., Arch Biochem Biophys, 1994, 311(1): 144-52). Lubricin acts as a chondroprotective barrier against direct solid-to-solid contact in joints when the kinematic conditions are conducive to surface sliding in the boundary lubrication regime, characterized by the formation of an adsorbed molecular layer conformal with the articular tissue surface topography (see Neu, C. P., K. Komvopoulos, and A. H. Reddi, Tissue Engineering, Part B: Reviews, 2008). In the absence of a strongly adsorbing, continuous, self-replenishing boundary lubricant layer, intermittent asperity-asperity interactions lead to rapid deterioration of the join surface by various mechanical wear processes, such as adhesion, abrasion, surface fatigue, and delamination. Lubricin tribosupplementation has been shown to reduce cartilage degeneration (see Jay, G. D., et al., Arthritis and rheumatism, 2012, 64(4): 1162-71, and Teeple, E., et al., The American Journal of Sports Medicine, 2011, 39(1): 164-72). Reducing friction at the articular cartilage interface will suppress cartilage wear and surface damage.

Another extracellular matrix is the vitreous humor, a complex gel-like network which fills the posterior cavity of the eye, is composed of approximately 99 wt % water, 0.9 wt % salts, less than 0.1 wt % heterotypic collagen fibrils (type II, V/XI and IX), and a hyaluronan network. It serves several purposes (including developmental, optical, protective) and its degradation has been implicated in several ocular pathologies, such as retinal tear, retinal detachment, retinal edema, choroidal detachment, vitreous hemorrhage, and glaucoma.

In addition, degeneration of the nucleus pulposus, a gel-like substance is the inner core of the spinal disc, results in reduced ability of the spinal disc to transmit loads evenly and efficiently between vertebral bodies, and leads to damage in the annular region of the disc, known as the annulus fibrosis. The nucleus pulposus functions to distribute hydraulic pressure in all directions within each disc under compressive loads and is comprised of chondrocyte-like cells, collagen fibrils, and proteoglycan aggrecans that aggregate through hyaluronic chains. Fissures or tears in the annulus can translate into a disc that herniates or ruptures, resulting in impingement of the nerves in the region of the disc and finally lower back or leg pain.

This disclosure provides extracellular matrix-binding synthetic peptidoglycans for use in supplementing and/or replacing extracellular matrix fluids in the body, thus treating and/or preventing diseases or disorders resulting from the degradation thereof.

SUMMARY

Provided herein is an extracellular matrix-binding synthetic peptidoglycan, wherein the extracellular matrix-binding synthetic peptidoglycan comprises a glycan; from about 1 to 60 collagen binding peptide(s); and from about 1 to 60 hyaluronic acid binding peptide(s). In the extracellular matrix-binding synthetic peptidoglycan, the collagen binding peptide(s) and the hyaluronic acid binding peptide(s) are covalently bonded to the glycan. The synthetic peptidoglycan can comprise any glycan, including, but not limited to, dextran, chondroitin, chondroitin sulfate, dermatan, dermatan sulfate, heparan, heparin, keratin, keratan sulfate, or hyaluronic acid.

Also provided is a pharmaceutical composition comprising an extracellular matrix-binding synthetic peptidoglycan comprising a glycan; from about 1 to 80 collagen binding peptide(s); and from about 1 to 80 hyaluronic acid binding peptide(s), wherein the collagen binding peptide(s) and the hyaluronic acid binding peptide(s) are covalently bonded to the glycan.

Synthetic peptidoglycans as described herein may be useful in supplementing and/or protecting tissues that have both collagen and hyaluronic acid, such as cartilage, the nucleus pulposus, and the vitreous humor of the eye. Accordingly, provided is a method of treating and/or preventing cartilage degeneration in a patient comprising administering to a patient in need thereof a pharmaceutical composition comprising the extracellular matrix-binding synthetic peptidoglycan described herein. In addition, provided is a method of treating and/or preventing vitreous humor degeneration in a patient comprising administering to a patient in need thereof the pharmaceutical composition comprising the extracellular matrix-binding synthetic peptidoglycan described herein. Also provided is a method of treating and/or preventing nucleus pulposus degeneration in a patient comprising administering to a patient in need thereof the pharmaceutical composition comprising the extracellular matrix-binding synthetic peptidoglycan described herein.

It is further contemplated that the extracellular matrix-binding synthetic peptidoglycans and pharmaceutical compositions thereof can be used in vascular intervention procedures including, for example, to prevent any one or a combination of platelet binding to exposed collagen of the denuded endothelium, platelet activation, thrombosis, inflammation resulting from denuding the endothelium, intimal hyperplasia, and vasospasm. The extracellular matrix-binding synthetic peptidoglycans described herein can also be used to stimulate endothelial cell proliferation and can bind to collagen in a denuded vessel.

BRIEF DESCRIPTION OF THE DRAWINGS

Certain aspects are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
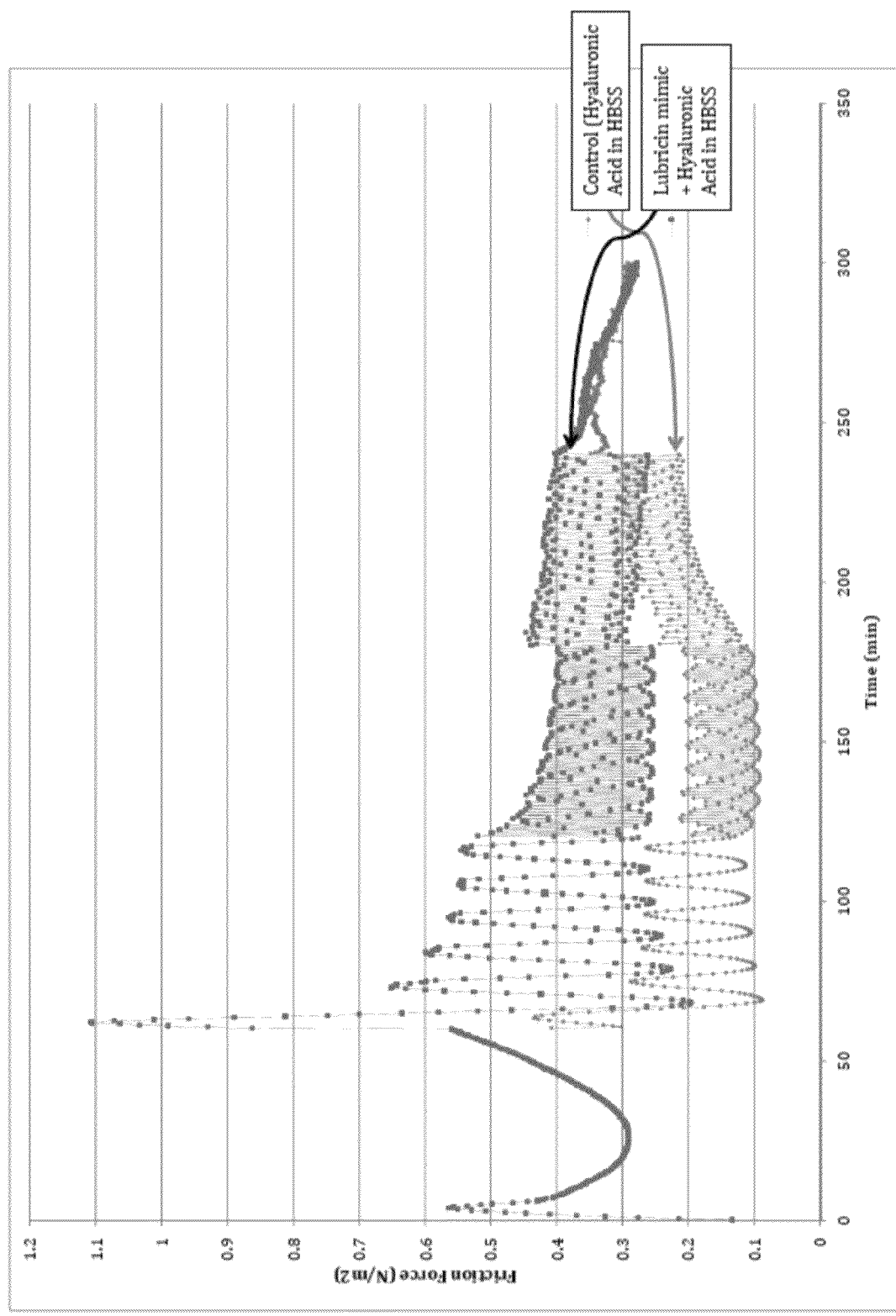
FIG. 1 shows the frictional force in the case of undamaged cartilage (with no aggrecan depletion) and shows that with a synthetic peptidoglycan according to according to the disclosure, the friction increases between the cartilage surfaces.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a peptide" includes a plurality of peptides.

DEFINITIONS

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "synovial cavity" refers to the space between the bones of a synovial joint that is filled with synovial fluid.

As used herein, the term "treating and/or preventing" refers to preventing, curing, reversing, attenuating, alleviating, minimizing, suppressing or halting the deleterious effects of a disease state, disease progression or other abnormal condition.

As used herein, the term "patient" refers to a subject (i.e., human) at risk for or suffering from a disease state, disease progression or other abnormal or deleterious condition.

As used herein, the term "synthetic peptidoglycan" refers to a synthetic conjugate that comprises a glycan and one or more synthetic peptides covalently bonded thereto. The glycan portion can be made synthetically or derived from animal sources. The synthetic peptides can be covalently bonded directly to the glycan or via a linker. For methods of conjugating hyaluronic acid binding peptides to glycans, see, e.g., WO 2012/162534. For methods of conjugating collagen binding peptides to glycans, see, e.g., US 2013/0190246, US 2012/0100106, and US 2011/0020298, the disclosures of which are incorporated herein by reference in their entirety.

As used herein, the term "covalently bonded" refers to a bond in which one or more pairs of electrons are shared by two atoms.

As used herein, the term "glycan" refers a compounds consisting of a large number of monosaccharides linked glycosidically. In certain embodiments, the glycan is a glycosaminoglycans, which comprise 2-amino sugars linked in an alternating fashion with uronic acids, and include polymers such as heparin, heparan sulfate, chondroitin, keratin, and dermatan. Accordingly, non-limiting examples of glycans which can be used in the embodiments described herein include alginate, agarose, dextran, chondroitin, chondroitin sulfate, dermatan, dermatan sulfate, heparan, heparin, keratin, keratan sulfate, and hyaluronic acid.

As used herein, "hyaluronic acid binding peptide" refers to a synthetic peptide comprising a hyaluronic acid binding sequence. In the various embodiments described herein, the peptide component of the synthetic peptidoglycan can comprise an amino acid sequence selected from the group consisting of: GAHWQFNALTVR (SEQ ID NO: 1), GAHWQFNALTVRGG (SEQ ID NO: 2), GDRRRRRMWHRQ (SEQ ID NO: 3), GKHLGGKHRRSR (SEQ ID NO: 4), RGTHHAQKRRS (SEQ ID NO: 5), RRHKSGHIQGSK (SEQ ID NO: 6), SRMHGRVRGRHE (SEQ ID NO: 7), RRRAGLTAGRPR (SEQ ID NO: 8), RYGGHRTSRKWV (SEQ ID NO: 9), RSARYGHRRGVG (SEQ ID NO: 10), GLRGNRRVFARP (SEQ ID NO: 11), SRGQRGRLGKTR (SEQ ID NO: 12), DRRGRSSLPKLAGPVEFPDRKIKGRR (SEQ ID NO: 13), RMRRKGRVKHWG (SEQ ID NO: 14), RGGARGRHKTGR (SEQ ID NO: 15), TGARQRGLQGGWGPRHLRGKDQPPGR (SEQ ID NO: 16), RQRRRDLTRVEG (SEQ ID NO: 17), STKDHNRGRRNVGPVSRSTLRDPIRR (SEQ ID NO: 18), RRIGHQVGGRRN (SEQ ID NO: 19), RLESRAAGQRRA (SEQ ID NO: 20), GGPRRHLGRRGH (SEQ ID NO: 21), VSKRGHRRTAHE (SEQ ID NO: 22), RGTRSGSTR (SEQ ID NO: 23), RRRKKIQGRSKR (SEQ ID NO: 24), RKSYGKYQGR (SEQ ID NO: 25), KNGRYSISR (SEQ ID NO: 26), RRRCGQKKK (SEQ ID NO: 27), KQKIKHVVKLK (SEQ ID NO: 28), KLKSQLVKRK (SEQ ID NO: 29), RYPISRPRKR (SEQ ID NO: 30), KVGKSPPVR (SEQ ID NO: 31), KTFGKMKPR (SEQ ID NO: 32), RIKWSRVSK (SEQ ID NO: 33) or KRTMRPTRR (SEQ ID NO: 34), or any peptide sequence comprising a sequence with at least about 80% sequence identity to the amino acid sequence. Additional peptides that can be included as the peptide component of the hyaluronic acid binding synthetic peptidoglycans include peptides which have an Arg-Arg (R—R) motif, such as one or more peptides selected from the group consisting of RRASRSRGQVGL (SEQ ID NO: 35), GRGTHHAQKRRS (SEQ ID NO: 36), QPVRRLGTPVVG (SEQ ID NO: 37), ARRAEGKTRMLQ (SEQ ID NO: 38), PKVRGRRHQASG (SEQ ID NO: 39), SDRHRRRREADG (SEQ ID NO: 40), NQRVRRVKHPPG (SEQ ID NO: 41), RERRERHAVARHGPGLERDARNLARR (SEQ ID NO: 42), TVRPGGKRGGQVGPPAGVLHGRRARS (SEQ ID NO: 43), NVRSRRGHRMNS (SEQ ID NO: 44), DRRRGRTRNIGN (SEQ ID NO: 45), KTAGHGRRWSRN (SEQ ID NO: 46), AKRGEGRREWPR (SEQ ID NO: 47), GGDRRKAHKLQA (SEQ ID NO: 48), RRGGRKWGSFEG (SEQ ID NO: 49) and RQRRRDLTRVEG (SEQ ID NO: 50) (see, e.g., Amemiya et al, Biochem. Biophys. Acta, 2005, 1724, 94-99, incorporated herein by reference). In another embodiment, the peptide is selected from the group consisting of RDGTRYVQKGEYR (SEQ ID NO: 51), HREARSGKYK (SEQ ID NO: 52), PDKKHKLYGV (SEQ ID NO: 53), and WDKERSRYDV (SEQ ID NO: 54) (see, e.g., Yang et al, EMBO Journal, 1994, 13, 286-296, and Goetinck et al, J. Cell. Biol, 1987, 105, 2403-2408, both of which are incorporated herein by reference).

As used herein, the term "collagen binding peptide" refers to a synthetic peptide comprising a collagen binding sequence. The "collagen binding peptide" can have amino acid homology with a portion of a protein normally or not normally involved in collagen fibrillogenesis. In one embodiment, the collagen binding peptide comprises from about 5 to about 40 amino acids, or from about 5 to about 20 amino acids, or from about 5 to about 10 amino acids. In some embodiments, these peptides have homology or sequence identity to the amino acid sequence of a small leucine-rich proteoglycan, a platelet receptor sequence, or a protein that regulates collagen fibrillogenesis. In various embodiments, the collagen binding peptide comprises an amino acid sequence selected from the group consisting of RRANAALKAGELYKSILY (SEQ ID NO: 55), RLDGNEIKR (SEQ ID NO: 56), AHEEISTTNEGVM (SEQ ID NO: 57), GELYKSILY (SEQ ID NO: 58), NGVFKYRPRYFLYKHAYFYPPLKRFPVQ (SEQ ID NO: 59), CQDSETRTFY (SEQ ID NO: 60), TKKTLRT (SEQ ID NO: 61), GLRSKSKKFRRPDIQYPDATDEDITSHM (SEQ ID NO: 62), SQNPVQP (SEQ ID NO: 63), SYIRIADTNIT (SEQ ID NO: 64), KELNLVYT (SEQ ID NO: 65), GSITTIDVPWNVGC (SEQ ID NO: 66), and GSITTIDVPWNV (SEQ ID NO: 67) any peptide sequence comprising a sequence with at least about 80% sequence identity to the amino acid sequence. In certain embodiments, the collagen binding peptide comprises an amino acid sequence that has about 80%, about 85%, about 90%, about 95%, about 98%, or about 100% sequence identity with the collagen binding domain(s) of the von Willebrand factor or a platelet collagen receptor as described in Chiang, et al. J. Biol. Chem. 277: 34896-34901 (2002), Huizinga, et al., Structure 5: 1147-1156 (1997), Romijn, et al., J. Biol. Chem. 278: 15035-15039 (2003), and Chiang, et al., Cardio. & Haemato. Disorders-Drug Targets 7: 71-75 (2007), each incorporated herein by reference.

In any of the embodiments described herein, any one or more of the synthetic peptides (e.g., the hyaluronic acid binding peptide and/or the collagen binding peptide) may have a glycine-cysteine (GC) attached to the C-terminus of the peptide, and/or a glycine-cysteine-glycine (GCG) attached to the N-terminus of the peptide. For example, the collagen binding peptide may comprise an amino acid sequence selected from the group consisting of RRANAALKAGELYKSILYGC (SEQ ID NO: 68), RLDGNEIKRGC (SEQ ID NO: 69), AHEEISTTNEGVMGC (SEQ ID NO: 70), GCGGELYKSILY (SEQ ID NO: 71), NGVFKYRPRYFLYKHAYFYPPLKRFPVQGC (SEQ ID NO: 72), CQDSETRTFYGC (SEQ ID NO: 73), TKKTLRTGC (SEQ ID NO: 74), GLRSKSKKFRRPDIQYPDATDEDITSHMGC (SEQ ID NO: 75), SQNPVQPGC (SEQ ID NO: 76), SYIRIADTNITGC (SEQ ID NO: 77), KELNLVYTGC (SEQ ID NO: 78), GSITTIDVPWNVGC (SEQ ID NO: 66), GCGGELYKSILYGC (SEQ ID NO: 79) and GELYKSILYGC (SEQ ID NO: 80).

As used herein, the term "amino acid" refers to either a natural and/or unnatural or synthetic amino acid, including glycine and both the D and L optical isomers, amino acid analogs and peptidomimetics. Single letter and three letter abbreviations of the naturally occurring amino acids are listed below in Table 1. A peptide of three or more amino acids is commonly called an oligopeptide if the peptide chain is short. If the peptide chain is long, the peptide is commonly called a polypeptide or a protein.

TABLE 1

| 1-Letter | 3-Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

In any of the embodiments described herein, a synthetic peptide (e.g., a hyaluronic acid binding peptide and/or a collagen binding peptide) comprises any amino acid sequence described in the preceding paragraph or an amino acid sequence with 80%, 85%, 90%, 95%, 98%, or 100% homology to any of these amino acid sequences. In various embodiments, the peptide components of the synthetic peptidoglycan described herein can be modified by the inclusion of one or more conservative amino acid substitutions. As is well-known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions are possible provided that these do not excessively affect the hyaluronic acid binding activity of the peptide.

As used herein, the term "homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A peptide (or a polypeptide or peptide region) has a certain percentage (for example, 60%, 65%, 70%, 75%, 80%, 85%, 90%, 95%, 98% or 99%) of "homology" or "sequence identity" to another sequence means that, when aligned, that percentage of bases (or amino acids) are the same in comparing the two sequences. This alignment and the percent homology or sequence identity can be determined using software programs known in the art (e.g., BLAST), and for example, those described in Ausubel et al. eds. (2007) Current Protocols in Molecular Biology.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table 2.

TABLE 2

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In one embodiment, the synthetic peptidoglycans of the disclosure bind, either directly or indirectly to collagen and/or hyaluronic acid. The terms "binding" or "bind" as used herein are meant to include interactions between molecules that may be detected using, for example, a hybridization assay, surface plasmon resonance, ELISA, competitive binding assays, isothermal titration calorimetry, phage display, affinity chromatography, rheology or immunohistochemistry. The terms are also meant to include "binding" interactions between molecules. Binding may be "direct" or "indirect". "Direct" binding comprises direct physical contact between molecules. "Indirect" binding between molecules comprises the molecules having direct physical contact with one or more molecules simultaneously. For example, it is contemplated that synthetic peptidoglycans of the disclosure directly bind and interact with both hyaluronic acid and type II collagen, and can be used to restore the low friction properties of articular cartilage, thus protect the surface from mechanical wear. This binding can result in the formation of a "complex" comprising the interacting molecules. A "complex" refers to the binding of two or more molecules held together by covalent or non-covalent bonds, interactions or forces.

Synthetic Peptidoglycans

The present disclosure provides an extracellular matrix-binding synthetic peptidoglycan comprising: a) a glycan; b) from about 1 to about 80 collagen binding peptide(s); and c) from about 1 to about 80 hyaluronic acid binding peptide(s); wherein the peptides of b) and c) are covalently bonded to the glycan.

In the synthetic peptidoglycan disclosed herein, the glycan can be any glycan, or polysaccharide, including but not limited to, dextran, chondroitin, chondroitin sulfate, dermatan, dermatan sulfate, heparan, heparin, keratin, keratan sulfate, and hyaluronic acid. In some embodiments, the glycan is chondroitin sulfate. In some embodiments, the glycan is dermatan sulfate. In some embodiments, the glycan is hyaluronic acid.

The peptides can be bonded to the glycan directly or via a linker. In certain embodiments, the peptides are covalently bonded to the glycan via a linker. The linker can be any suitable bifunctional linker, e.g., 3-(2-pyridyldithio)propionyl hydrazide (PDPH), N-[β-maleimidopropionic acid]hydrazide (BMPH), and the like. In any of the various embodiments described herein, the sequence of the peptide may be modified to include a glycine-cysteine segment to provide an attachment point for a glycan. In certain embodiments, the linker is N-[β-maleimidopropionic acid]hydrazide (BMPH).

Depending on the desired properties of the synthetic peptidoglycan, the total number of peptides bound to the glycan can be varied. In certain embodiments, the total number of peptides present in the synthetic peptidoglycan is from about 2 to about 160, from about 10 to about 160, from about 20 to about 160, from about 30 to about 160, from about 40 to about 160, from about 40 to about 150, from about 40 to about 140, from about 10 to about 120, or from about 20 to about 110, or from about 20 to about 100, or from about 20 to about 90, or from about 30 to about 90, or from about 40 to about 90, or from about 50 to about 90, or from about 50 to about 80, or from about 60 to about 80, or about 10, or about 20, or about 30, or about 40, or about 50, or about 60, or about 70, or about 80, or about 90, or about 100, or about 110, or about 120. In certain embodiments, the total number of peptides present in the synthetic peptidoglycan is less than about 50. In certain embodiments, the total number of peptides present in the synthetic peptidoglycan is from about 10 to about 40. In certain embodiments, the total number of peptides present in the synthetic peptidoglycan is about 22. In certain embodiments, the total number of collagen binding peptides is from about 5 to about 20, or about 10, or about 11. In certain embodiments, the total number of hyaluronic acid binding peptides is from about 5 to about 20, or about 10, or about 11.

In one aspect, the collagen binding peptides present in the extracellular matrix-binding synthetic peptidoglycans described herein comprise have binding affinity to one or more of collagen types I, II, III, or IV. One or more collagen binding peptide having a specified binding affinity can be used in the extracellular matrix-binding synthetic peptidoglycans described herein. For example, the extracellular matrix-binding synthetic peptidoglycans can comprise at least one collagen binding peptide which has binding affinity to type I collagen and at least one collagen binding peptide which has binding affinity to type II collagen. In another aspect, the collagen binding peptides have binding affinity to type I collagen. In certain aspects, the collagen binding peptides have binding affinity to type II collagen.

Suitable collagen binding peptides are known in the art (see, e.g., US 2013/0190246, US 2012/0100106, and US 2011/0020298, the disclosures of which are incorporated herein by reference in their entirety). In one embodiment, the collagen binding peptide comprises from about 5 to about 40 amino acids. In some embodiments, these peptides have homology to the amino acid sequence of a small leucine-rich proteoglycan, a platelet receptor sequence, or a protein that regulates collagen fibrillogenesis.

In various embodiments, the collagen binding peptide comprises an amino acid sequence selected from the group consisting of WYRGRLGC (SEQ ID NO: 81), RRANAALKAGELYKSILYGC (SEQ ID NO: 68), RLDGNEIKRGC (SEQ ID NO: 69), AHEEISTTNEGVMGC (SEQ ID NO: 70), GCGGELYKSILY (SEQ ID NO: 71), NGVFKYRPRYFLYKHAYFYPPLKRFPVQGC (SEQ ID NO: 72), CQDSETRTFY (SEQ ID NO: 60), TKKTLRTGC (SEQ ID NO: 74), GLRSKSKKFRRPDIQYPDATDEDITSHMGC (SEQ ID NO: 75), SQNPVQPGC (SEQ ID NO: 76), SYIRIADTNITGC (SEQ ID NO: 77), SYIRIADTNIT (SEQ ID NO: 64), KELNLVYT (SEQ ID NO: 65), KELNLVYTGC (SEQ ID NO: 78), GSITTIDVPWNV (SEQ ID NO: 67), GELYKSILYGC (SEQ ID NO: 80) and GSITTIDVPWNVGC (SEQ ID NO: 66), or any peptide sequence comprising a sequence with at least about 80% sequence identity, or at least about 80% sequence identity, or at least about 85% sequence identity, or at least about 90% sequence identity, or at least about 95% sequence identity, or at least about 98% sequence identity. In certain embodiments, the collagen binding peptide is WYRGRLGC (SEQ ID NO: 81), or any peptide that has at least about 80% sequence identity, or at least about 85% sequence identity, or at least about 90% sequence identity, or at least about 95% sequence identity, or at least about 98% sequence identity. In certain embodiments, the collagen binding peptide is about 80%, about 85%, about 90%, about 95%, about 98%, or about 100% homologous with the collagen binding domain(s) of the von Willebrand factor or a platelet collagen receptor as described in Chiang, et al. J. Biol. Chem. 277: 34896-34901 (2002), Huizing a, et al., Structure 5: 1147-1156 (1997), Romijn, et al., J. Biol. Chem. 278: 15035-15039 (2003), and Chiang, et al., Cardio. & Haemato. Disorders-Drug Targets 7: 71-75 (2007), each incorporated herein by reference.

Suitable hyaluronic acid binding peptides are known in the art (see, e.g., WO 2012/162534). In the various embodiments described herein, the peptide component of the synthetic peptidoglycan can comprise an amino acid sequence selected from the group consisting of GAHWQFNALTVRGG (SEQ ID NO: 2), GDRRRRRMWHRQ (SEQ ID NO: 3), GKHLGGKHRRSR (SEQ ID NO: 4), RGTHHAQKRRS (SEQ ID NO: 5), RRHKSGHIQGSK (SEQ ID NO: 6), SRMHGRVRGRHE (SEQ ID NO: 7), RRRAGLTAGRPR (SEQ ID NO: 8), RYGGHRTSRKWV (SEQ ID NO: 9), RSARYGHRRGVG (SEQ ID NO: 10), GLRGNRRVFARP (SEQ ID NO: 11), SRGQRGRLGKTR (SEQ ID NO: 12), DRRGRSSLPKLAGPVEFPDRKIKGRR (SEQ ID NO: 13), RMRRKGRVKHWG (SEQ ID NO: 14), RGGARGRHKTGR (SEQ ID NO: 15), TGARQRGLQGGWGPRHLRGKDQPPGR (SEQ ID NO: 16), RQRRRDLTRVEG (SEQ ID NO: 17), STKDHNRGRRNVGPVSRSTLRDPIRR (SEQ ID NO: 18), RRIGHQVGGRRN (SEQ ID NO: 19), RLESRAAGQRRA (SEQ ID NO: 20), GGPRRHLGRRGH (SEQ ID NO: 21), VSKRGHRRTAHE (SEQ ID NO: 22), RGTRSGSTR (SEQ ID NO: 23), RRRKKIQGRSKR (SEQ ID NO: 24), RKSYGKYQGR (SEQ ID NO: 25), KNGRYSISR (SEQ ID NO: 26), RRRCGQKKK (SEQ ID NO: 27), KQKIKHVVKLK (SEQ ID NO: 28), KLKSQLVKRK (SEQ ID NO: 29), RYPISRPRKR (SEQ ID NO: 30), KVGKSPPVR (SEQ ID NO: 31), KTFGKMKPR (SEQ ID NO: 32), RIKWSRVSK (SEQ ID NO: 33) and KRTMRPTRR (SEQ ID NO: 34), or any peptide sequence comprising a sequence with at least about 80% sequence identity, or at least about 80% sequence identity, or at least about 85% sequence identity, or at least about 90% sequence identity, or at least about 95% sequence identity, or at least about 98% sequence identity.

Additional peptides that can be included as the peptide component of the hyaluronic acid binding synthetic peptidoglycans include peptides which have an Arg-Arg (R-R) motif, such as one or more peptides selected from the group consisting of RRASRSRGQVGL (SEQ ID NO: 35), GRGTHHAQKRRS (SEQ ID NO: 36), QPVRRLGTPVVG (SEQ ID NO: 37), ARRAEGKTRMLQ (SEQ ID NO: 38), PKVRGRRHQASG (SEQ ID NO: 39), SDRHRRRREADG (SEQ ID NO: 40), NQRVRRVKHPPG (SEQ ID NO: 41), RERRERHAVARHGPGLERDARNLARR (SEQ ID NO: 42), TVRPGGKRGGQVGPPAGVLHGRRARS (SEQ ID NO: 43), NVRSRRGHRMNS (SEQ ID NO: 44), DRRRGRTRNIGN (SEQ ID NO: 45), KTAGHGRRWRN (SEQ ID NO: 46), AKRGEGRREWPR (SEQ ID NO: 47), GGDRRKAHKLQA (SEQ ID NO: 48), RRGGRKWGSFEG (SEQ ID NO: 49) and RQRRRDLTRVEG (SEQ ID NO: 50), or any peptide sequence comprising a sequence with at least about 80% sequence identity, or at least about 80% sequence identity, or at least about 85% sequence identity, or at least about 90% sequence identity, or at least about 95% sequence identity, or at least about 98% sequence identity (see, e.g., Amemiya et al, Biochem. Biophys. Acta, 2005, 1724, 94-99, incorporated herein by reference). In certain embodiments, the collagen binding peptide is GAHWQFNALTVRGG (SEQ ID NO: 2), or any peptide sequence comprising a sequence with at least about 80% sequence identity, or at least about 80% sequence identity, or at least about 85% sequence identity, or at least about 90% sequence identity, or at least about 95% sequence identity, or at least about 98% sequence identity. In another embodiment, the peptide is selected from the group consisting of RDGTRYVQKGEYR (SEQ ID NO: 51), HREARSGKYK (SEQ ID NO: 52), PDKKHKLYGV (SEQ ID NO: 53), and WDKERSRYDV (SEQ ID NO: 54) (see, e.g., Yang et al, EMBO Journal, 1994, 13, 286-296, and Goetinck et al, J. Cell. Biol., 1987, 105, 2403-2408, both of which are incorporated herein by reference).

In another embodiment, the hyaluronic acid binding peptide may be selected from a group consisting of the B-X7-B homology, in which B is either lysine or arginine and X is any non-acidic amino acid residue (i.e., any amino acid other than aspartic acid or glutamic acid), where at least one of the 7× residues is a basic residue (i.e., arginine, lysine, or histidine). Peptides may also be selected by phage display, utilizing positive selection for binding to hyaluronic acid. An hyaluronic acid binding peptide may be determined by its interaction with hyaluronic acid, and measured by any of the techniques used to evaluate molecular interactions. For example, surface plasmon resonance, ELISA, competitive binding assays, isothermal titration calorimetry, affinity chromatography, rheology or immunohistochemistry. Peptides that are considered "hyaluronic acid binding" may interact with hyaluronic acid or hyaluronic acid-containing tissues such that the interaction is not attributed to known chemically reactive groups. The interaction may be due to hydrophobic and charge interactions resulting from the amino acid residues in the peptide. The interaction may be measured by immobilizing hyaluronic acid on a microplate and incubating with hyaluronic acid binding peptides followed by detection techniques such as biotin-avidin with the use of a chromophore. The interaction may also be measured by mechanical influence on hyaluronic acid-containing fluids, gels, or tissues that have been incubated with the hyaluronic acid binding peptide, or with a peptidoglycan containing an hyaluronic acid binding peptide or peptides.

For identifying a peptide, a peptide selected from phage display, or one that is identified from a hyaluronic acid binding motif in a protein, can be synthesized and evaluated for its interaction with hyaluronic acid. For example, a B-X7-B sequence could be synthesized with a biotin modification at the N-terminus and incubated on a hyaluronic acid coated microplate. A dose response binding curve can be generated to determine the ability of the peptide to bind to hyaluronic acid.

Similarly for a collagen binding peptide, a synthetic peptide derived from a phage display library selected for collagen binding can be generated. The peptide can be synthesized and evaluated for binding to collagen by any of the techniques such as SPR, ELISA, ITC, affinity chromatography, or others known in the art. An example could be a biotin modified peptide sequence that is incubated on a microplate containing immobilized collagen. A dose response binding curve can be generated using a streptavidin-chromophore to determine the ability of the peptide to bind to collagen.

In one embodiment, provided herein is an extracellular matrix-binding synthetic peptidoglycan comprising:
a) chondroitin sulfate;
b) from about 1 to about 80 collagen binding peptide(s); and
c) from about 1 to about 80 hyaluronic acid binding peptide(s);
wherein the peptides of b) and c) are covalently bonded to the glycan; and further wherein the collagen binding peptide(s) are WYRGRLGC (SEQ ID NO: 81) and the hyaluronic acid binding peptide(s) are GAHWQFNALTVRGGGC (SEQ ID NO: 82). In certain embodiments, the peptides are covalently bonded to the glycan via a linker, such as N-[β-maleimidopropionic acid]hydrazide (BMPH).

In another embodiment, provided herein is an extracellular matrix-binding synthetic peptidoglycan comprising:
a) chondroitin sulfate;
b) from about 5 to about 20 collagen binding peptide(s); and
c) from about 5 to about 20 hyaluronic acid binding peptide(s);
wherein the peptides of b) and c) are covalently bonded to the glycan via N-[β-maleimidopropionic acid]hydrazide (BMPH); and further wherein the collagen binding peptide(s) are WYRGRLGC (SEQ ID NO: 81) and the hyaluronic acid binding peptide(s) are GAHWQFNALTVRGGGC (SEQ ID NO: 82).

In various embodiments described herein, the peptides described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions may too be possible, provided that they do not substantially affect the binding activity of the peptide (i.e., hyaluronic acid or collagen binding affinity).

In various embodiments described herein, the synthetic peptidoglycan is resistant to aggrecanase. An aggrecanase is characterized in the art as any enzyme known to cleave aggrecan. In one embodiment, the synthetic peptidoglycan does not contain a polymerizable group, such as methacrylates, ethacrylates, itaconates, acrylamides, thiols, peptides and aldehydes.

Synthesis of Peptidoglycans

The peptides used in the synthetic peptidoglycans described herein (i.e., the hyaluronic acid binding peptide and the collagen peptide) may be purchased from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification. Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

In certain embodiments, the peptides are covalently bonded to the glycan directly (i.e., without a linker). In such embodiments, the synthetic peptidoglycan may be formed by covalently bonding the peptides to the glycan through the formation of one or more amide, ester or imino bonds between an acid, aldehyde, hydroxy, amino, or hydrazo group on the glycan. All of these methods are known in the art or are further described in the Examples section of this application or in Hermanson G. T., Bioconjugate Techniques, Academic Press, pp. 169-186 (1996), incorporated herein by reference. As shown in Scheme 1, the glycan (e.g., "CS") can be oxidized using a periodate reagent, such as sodium periodate, to provide aldehyde functional groups on the glycan (e.g., "ox-CS") for covalently bonding the peptides to the glycan. In such embodiments, the peptides may be covalently bonded to a glycan by reacting a free amino group of the peptide with an aldehyde functional groups of the oxidized glycan, e.g., in the presence of a reducing agent, utilizing methods known in the art.

In embodiments where the peptides are covalently bonded to the glycan via a linker, the oxidized glycan (e.g., "ox-CS") can be reacted with a linker (e.g., any suitable bifunctional liker, such as 3-(2-pyridyldithio)propionyl hydrazide (PDPH) or N-[β-maleimidopropionic acid]hydrazide (BMPH)) prior to contacting with the peptides. The linker typically comprises about 1 to about 30 carbon atoms, or about 2 to about 20 carbon atoms. Lower molecular weight linkers (i.e., those having an approximate molecular weight of about 20 to about 500) are typically employed. In addition, structural modifications of the linker are contemplated. For example, amino acids may be included in the linker, including but not limited to, naturally occurring amino acids as well as those available from conventional synthetic methods, such as beta, gamma, and longer chain amino acids.

As shown in Scheme 1, in one embodiment, the peptides are covalently bonded to the glycan (e.g., "CS") by reacting an aldehyde function of the oxidized glycan (e.g., "ox-CS") with 3-(2-pyridyldithio)propionyl hydrazide (PDPH) or N-[β-maleimidopropionic acid]hydrazide (BMPH) to form an glycan intermediate (e.g., "BMPH-CS") and further reacting the glycan intermediate with peptides containing at least one free thiol group (i.e., —SH group) to yield the synthetic peptidoglycan. In yet another embodiment, the sequence of the peptides may be modified to include an amino acid residue or residues that act as a spacer between the HA- or Collagen-binding peptide sequence and a terminating cysteine (C). For example a glycine-cysteine (GC) or a glycine-glycine-glycine-cysteine (GGGC) (SEQ ID NO: 83) or glycine-serine-glycine-cysteine (GSGC) (SEQ ID NO: 84) segment may be added to provide an attachment point for the glycan intermediate.

about 1 to about 80 hyaluronic acid binding peptide(s), such that the peptides are covalently bonded to the glycan.

The synthetic peptidoglycan can be synthesized by sequentially adding the peptides having different binding affinities to the glycan (i.e., oxidized glycan or glycan intermediate), or alternatively, adding all peptides simultaneously. The synthetic peptidoglycans can be isolated and/or purified using known methods, such as size exclusion chromatography, at any point in the synthesis.

Pharmaceutical Compositions and Administration

Disclosed herein is a pharmaceutical composition comprising the extracellular matrix-binding synthetic peptidoglycan, wherein the synthetic peptidoglycan comprises a glycan having from about 1 to about 80 collagen binding peptide(s) and from about 1 to about 80 hyaluronic acid binding peptide(s) covalently bonded to the glycan.

As is known in the art, the components as well as their relative amounts are determined by the intended use and method of delivery. The pharmaceutical compositions may be

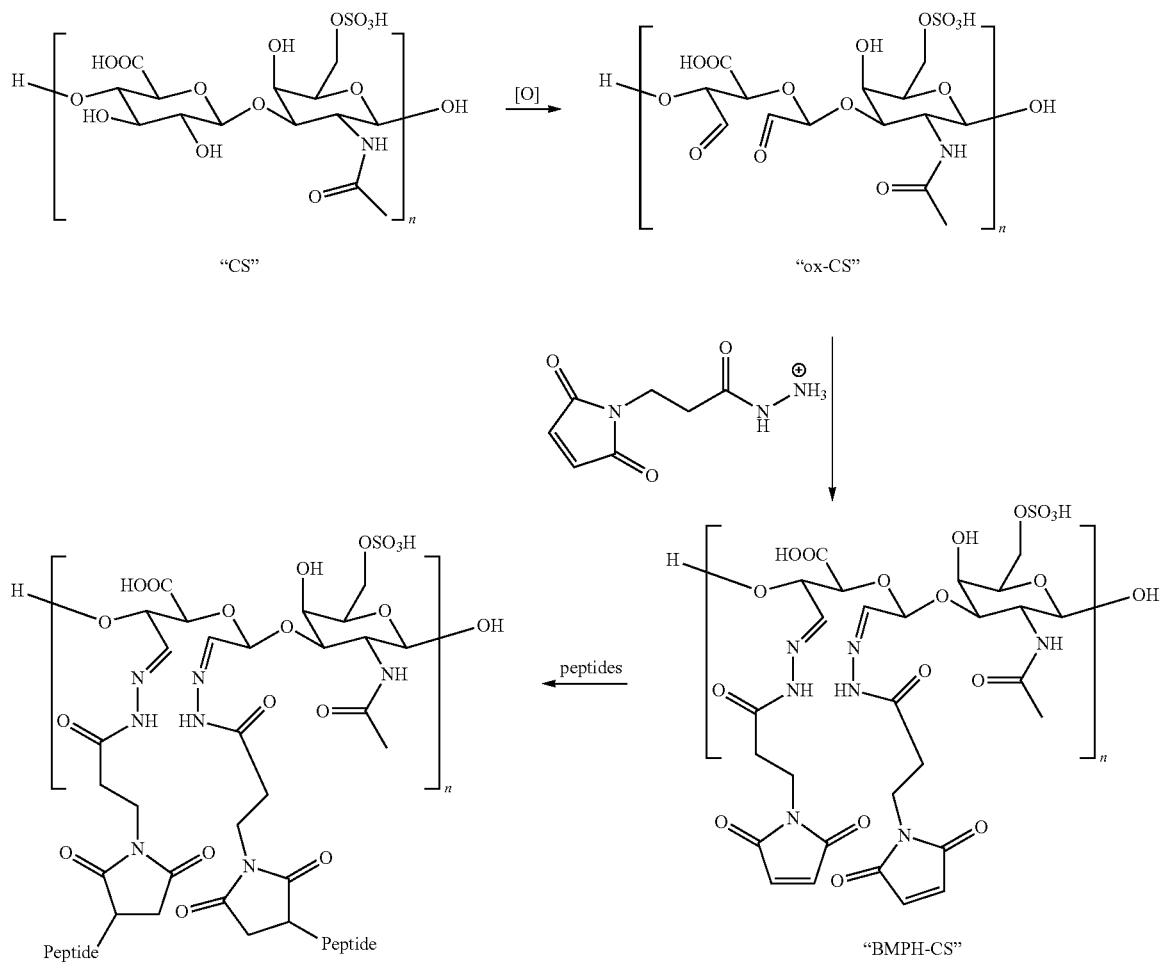

Scheme 1

Accordingly, in one embodiment, the synthetic peptidoglycans described herein are provided by a) oxidizing at least one vicinal diol group of a glycan to provide a glycan having at least two aldehyde functional groups; b) optionally reacting the glycan with a linker; and reacting the glycan with from about 1 to about 80 collagen binding peptide(s); and from for oral, topical or parenteral delivery, including intra-articular, intervertebral or intraocular delivery. In any of the embodiments described herein, the synthetic peptidoglycan can be administered alone or in combination with suitable pharmaceutical carriers or diluents. Diluent or carriers used in the pharmaceutical compositions can be selected so that they do not diminish the desired effects of the synthetic peptidoglycan. The pharmaceutical composition may be in any suitable form. Examples of suitable dosage forms include aqueous solutions, for example, a solution in isotonic saline, 5% glucose or other well-known pharmaceutically acceptable liquid carriers such as alcohols, glycols, esters and amides. In certain embodiments, the pharmaceutical composition further comprises one or more pH buffering agent, one or more ionic strength modifying agent, and/or one or more viscosity modulating agent.

In certain embodiments, the pharmaceutical composition further comprises a collagen binding peptidoglycan. Suitable "collagen binding peptidoglycans" are described in the art (see, e.g., US 2013/0190246, US 2012/0100106, and US 2011/0020298). In certain embodiments, the collagen binding peptidoglycan comprises chondroitin sulfate conjugated to from about 1 to about 20 collagen binding peptide(s) as described herein. In certain embodiments, the collagen binding peptide(s) of the collagen binding peptidoglycan is WYRGRLGC (SEQ ID NO: 81).

In certain embodiments, the pharmaceutical composition further comprises a hyaluronic acid binding peptidoglycan. Suitable "hyaluronic acid binding peptidoglycans" are described in the art (see, e.g., WO 2012/162534). In certain embodiments, the hyaluronic acid binding peptidoglycan comprises chondroitin sulfate conjugated to from about 1 to about 20 hyaluronic acid binding peptide(s) as described herein. In certain embodiments, the hyaluronic acid binding peptide(s) of the hyaluronic acid binding peptidoglycan is GAHWQFNALTVRGGC (SEQ ID NO: 82).

Suitable pH buffering agents for use in the pharmaceutical compositions herein described include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

Suitable ionic strength modifying agents include, for example, glycerin, propylene glycol, mannitol, glucose, dextrose, sorbitol, sodium chloride, potassium chloride, and other electrolytes.

Suitable viscosity modulating agents include but are not limited to, ionic and non-ionic water soluble polymers; crosslinked acrylic acid polymers such as the "carbomer" family of polymers, e.g., carboxypolyalkylenes that may be obtained commercially under the Carbopol™ trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or basic agent are employed in order to facilitate achieving the desired pH of the formulation.

In some embodiments, the synthetic peptidoglycans can be combined with minerals, amino acids, sugars, peptides, proteins, vitamins (such as ascorbic acid), or laminin, collagen, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic.

Parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known in the art.

In certain embodiments, the solubility of the synthetic peptidoglycan may need to be enhanced. In such cases, the solubility may be increased by the use of appropriate formulation techniques, such as the incorporation of solubility-enhancing compositions such as mannitol, ethanol, glycerin, polyethylene glycols, propylene glycol, poloxomers, and others known in the art.

The synthetic peptidoglycan may be sterilized to remove unwanted contaminants including, but not limited to, endotoxins and infectious agents. Sterilization techniques which do not adversely affect the structure and biotropic properties of the synthetic peptidoglycan can be used. In certain embodiments, the synthetic peptidoglycan can be disinfected and/or sterilized using conventional sterilization techniques including propylene oxide or ethylene oxide treatment, sterile filtration, gas plasma sterilization, gamma radiation, electron beam, and/or sterilization with a peracid, such as peracetic acid. In one embodiment, the synthetic peptidoglycan can be subjected to one or more sterilization processes. Alternatively, the synthetic peptidoglycan may be wrapped in any type of container including a plastic wrap or a foil wrap, and may be further sterilized.

In various embodiments, the synthetic peptidoglycan can be administered intravenously or into muscle, for example. Suitable routes for parenteral administration include intravascular, intravenous, intraarterial, intramuscular, cutaneous, subcutaneous, percutaneous, intradermal, and intraepidermal delivery. Suitable means for parenteral administration include needle (including microneedle) injectors, infusion techniques, and catheter-based delivery.

In various embodiments described herein, formulations for parenteral administration may be formulated to be for immediate and/or modified release. Modified release formulations include delayed, sustained, pulsed, controlled, targeted and programmed release formulations. Thus, a synthetic peptidoglycan may be formulated as a solid, semi-solid, or thixotropic liquid for administration as an implanted depot providing modified release of the active compound. Illustrative examples of such formulations include drug-coated stents and copolymeric (dl-lactic, glycolic)acid (PGLA) microspheres. In another embodiment, the synthetic peptidoglycan or composition comprising the synthetic peptidoglycan may be continuously administered, where appropriate.

In any of the embodiments described herein, the synthetic peptidoglycan or composition comprising the synthetic peptidoglycan can be administered intravascularly into the patient (e.g., into an artery or vein) in any suitable way. In various embodiments described herein, the synthetic peptidoglycan or composition comprising the synthetic peptidoglycan can be administered into a vessel of a patient prior to, during, or after vascular intervention. In various embodiments, vascular interventions, such as percutaneous coronary intervention (PCI), can include, for example, stenting, atherectomy, grafting, and angioplasty, such as balloon angioplasty. Illustratively, the vascular intervention can be one which involves temporarily occluding an artery, such as a coronary artery or a vein (e.g., balloon angioplasty), or it can be one which does not involve temporarily occluding an artery or a vein (e.g., non-balloon angioplasty procedures, stenting procedures that do not involve balloon angioplasty, etc.). Illustrative modes of delivery can include a catheter, parenteral administration, a coating on a balloon, through a porous balloon, a coated stent, and any combinations thereof or any other known methods of delivery of drugs during a vascular intervention procedure. In one illustrative embodiment, the target vessel can include a coronary artery, e.g., any blood vessel which supplies blood to the heart tissue of a patient, including native coronary arteries as well as those which have been grafted into the patient, for example, in an earlier coronary artery bypass procedure.

Exemplary pharmaceutical compositions for use with the synthetic peptidoglycans for parenteral administration or catheter-based delivery may comprise: a) a synthetic peptidoglycan as described herein; b) a pharmaceutically acceptable pH buffering agent to provide a pH in the range of about pH 4.5 to about pH 9; c) an ionic strength modifying agent in the concentration range of about 0 to about 300 millimolar; and d) water soluble viscosity modifying agent in the concentration range of about 0.25% to about 10% total formula weight or any individual component a), b), c), or d) or any combinations of a), b), c) and d).

Suitable dosages of the synthetic peptidoglycan can be determined by standard methods, for example by establishing dose-response curves in laboratory animal models or in clinical trials and can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, an effective dose ranges from about 1 ng/kg to about 10 mg/kg, 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In other illustrative aspects, effective doses ranges from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In any of the various embodiments described herein, effective doses ranges from about 0.01 µg to about 1000 mg per dose, 1 µg to about 100 mg per dose, about 100 µg to about 1.0 mg, about 50 µg to about 600 µg, about 50 µg to about 700 µg, about 100 µg to about 200 µg, about 100 µg to about 600 µg, about 100 µg to about 500 µg, about 200 µg to about 600 µg, or from about 100 µg to about 50 mg per dose, or from about 500 µg to about 10 mg per dose or from about 1 mg to 10 mg per dose. In other illustrative embodiments, effective doses can be 1 µg, 10 µg, 25 µg, 50 µg, 75 µg, 100 µg, 125 µg, 150 µg, 200 µg, 250 µg, 275 µg, 300 µg, 350 µg, 400 µg, 450 µg, 500 µg, 550 µg, 575 µg, 600 µg, 625 µg, 650 µg, 675 µg, 700 µg, 800 µg, 900 µg, 1.0 mg, 1.5 mg, 2.0 mg, 10 mg, 100 mg, or 100 mg to 30 grams.

Any effective regimen for administering the synthetic peptidoglycan can be used. For example, the synthetic peptidoglycan can be administered as a single dose, or as a multiple-dose daily regimen. Further, a staggered regimen, for example, one to five days per week can be used as an alternative to daily treatment.

In various embodiments described herein, the patient is treated with multiple injections of the synthetic peptidoglycan. In one embodiment, the patient is injected multiple times (e.g., about 2 up to about 50 times) with the synthetic peptidoglycan, for example, at 12-72 hour intervals or at 48-72 hour intervals. Additional injections of the synthetic peptidoglycan can be administered to the patient at an interval of days or months after the initial injections(s).

Methods

The synthetic peptidoglycans described herein may be useful in replacing, rejuvenating, or supplementing tissues that have both collagen and hyaluronic acid, such as cartilage, synovial fluid, and the vitreous humor.

Cartilage Degeneration

A well-lubricated surface on articular cartilage leads to optimal functionality of synovial joints. As occurs in osteoarthritis, however, a reduced lubrication results in cartilage degradation and fibrillation; which in turn contribute to joint dysfunction and pain. Reduced lubrication also leads to joint dysfunction and pain in other forms of arthritis, including rheumatoid arthritis.

As shown in Example 2, the synthetic peptidoglycans provided herein can be used to mimic some of the functions of lubricin, a mucinous glycoprotein secreted by tissues lining the interior surfaces of animal joints. The synthetic peptidoglycan thus has the potential to enhance lubrication at an articular cartilage surface, thereby reducing wear-induced erosion of the cartilage. The synthetic peptidoglycan also has the potential to protect macromolecules, like hyaluronic acid and type II collagen, from enzyme-induced degradation.

Accordingly, provided is a method of treating and/or preventing cartilage degeneration in a patient comprising administering to a patient in need thereof a pharmaceutical composition comprising the extracellular matrix-binding synthetic peptidoglycan described herein. In one embodiment, the patient is treated by injecting the pharmaceutical composition comprising the extracellular matrix-binding synthetic peptidoglycan into a synovial cavity.

It is also contemplated that the synthetic peptidoglycans can be used to treat and/or prevent articular cartilage disease by protecting the articular cartilage matrix from traumatic and cytokine-induced enzymatic degradation.

Vitreous Humor Degeneration

The vitreous humor is a viscoelastic, gel-like substance that fills the posterior cavity of the eye. Vitreous replacements have been used to replace a dysfunctional vitreous humor, for example in cases where opacification or the physical collapse and liquefaction of the vitreous has occurred, and as a temporary or permanent vitreous replacement during retinal surgery. A suitable vitreous replacement should be transparent, biocompatible, and they should have a density and refractive index close to the natural vitreous.

Accordingly, provided is a method of treating and/or preventing vitreous humor degeneration in a patient comprising administering to a patient in need thereof a pharmaceutical composition comprising the extracellular matrix-binding synthetic peptidoglycan described herein.

Nucleus Pulposus Degeneration

The nucleus pulposus is a gel-like substance present in spinal discs, and functions to distribute hydraulic pressure in all directions within each disc under compressive loads and is comprised of chondrocyte-like cells, collagen fibrils, and proteoglycan aggrecans that aggregate through hyaluronic chains. Degeneration of the nucleus pulposus results in reduced ability of the disc to transmit loads evenly and efficiently between vertebral bodies, and leads to damage in the annular region of the disc, known as the annulus fibrosis. Fissures or tears in the annulus can translate into a disc that herniates or ruptures, resulting in impingement of the nerves in the region of the disc and finally lower back or leg pain.

Attempts have also been made to replace only the nucleus pulposus. Replacement of the nucleus pulposus is expected to arrest the initial dehydration of the degenerated nucleus and return the disc to a fully hydrated state so that the degenerative process, including the associated pain, is postponed or prevented and the mechanical function is restored to the vertebral segment.

It is contemplated that the synthetic peptidoglycans described herein will bind to and protect the annulus fibrosis. Accordingly, provided is a method of treating and/or preventing annulus fibrosis degeneration in a patient comprising administering to a patient in need thereof a pharmaceutical composition comprising the extracellular matrix-binding synthetic peptidoglycan described herein. Also provided is a method of treating and/or preventing nucleus pulposus degeneration in a patient comprising administering to a patient in need thereof a pharmaceutical composition comprising the extracellular matrix-binding synthetic peptidoglycan described herein.

Table of abbreviations

The following abbreviations used herein have the following meanings.

| | |
|---|---|
| μg | Microgram |
| μm | Micrometer |
| BMPH | N-[β-maleimidopropionic acid]hydrazide |
| CS | Chondroitin sulfate |
| DNA | Deoxyribonucleic acid |
| HBSS | Hank's Balanced Salt Solution |
| HEPES | hydroxyethyl piperazineethanesulfonic acid |
| hr | Hour |
| Hz | Hertz |
| kg | Kilogram |
| M | Molar |
| M | Molar |
| m | Meter |
| MES | 2-ethanesulfonic acid |
| mg | Milligram |
| min | Minute |
| mL | Milliliter |
| mm | Millimeter |
| MOPS | 3-(N-morpholino)propanesulfonic acid |
| N | Newton |
| Pa | pascal |
| PBS | Phosphate buffered saline |
| PDPH | 3-(N-pyridyldithio)propionyl hydrazide |
| PIPES | piperazine-N,N'-bis(2-ethanesulfonic acid) |
| rad/s | radian per second |
| TAPS | 3-[[1,3-dihydroxy-2-(hydroxymethyl)propan2-yl]amino]propane-1-sulfonic acid |
| TES | 2-[[1,3-dihydroxy-2-(hydroxymethyl)propan2-yl]amino]ethanesulfonic acid |
| wt % | Weight percent |

EXAMPLES

Example 1

Synthesis of Peptidoglycans

Reagents

The peptides GAHWQFNALTVRGGGC (SEQ ID NO: 82) (GAH) and WYRGRLGC (SEQ ID NO: 81) (WYRGRL (residues 1-6 of SEQ ID NO: 81)) were purchased from Genscript (Piscataway, N.J.). N-[β-maleimidopropionic acid]hydrazide, trifluoroacetic acid salt (BMPH) was purchased from Pierce (Rockford, Ill.).

Methods

The synthesis of collagen type I and hyaluronic acid binding peptidoglycans has been previously described (see, e.g., Bernhard J. C., Panitch A. Acta Biomater 2012; 8: 1543-1550, and Paderi J. E., Panitch A. Biomacromolecules 2008; 9: 2562-2566). The present synthetic peptidoglycan was prepared according to the methods described therein and modified as follows.

Chondroitin sulfate (10 mg/mL) was oxidized with sodium meta-periodate in 0.1 M sodium acetate buffer pH 5.5. The degree of oxidation was controlled by the concentration of sodium meta-periodate. Heterobifunctional crosslinker BMPH was conjugated to functionalized chondroitin sulfate by reacting about 40-fold molar excess BMPH to chondroitin sulfate in 1×PBS pH 7.2 buffer at room temperature for 2 hours. The degree of functionalization was determined by measuring the consumption of BMPH during purification of CS-BMPH from excess BMPH. In the final step of conjugation, peptides WYRGRLGC (SEQ ID NO: 81) and GAHWQFNALTVRGGGC (SEQ ID NO: 82) were dissolved in water and each was added at one-half molar equivalent to the number of BMPH reactive groups on chondroitin. For example, chondroitin sulfate with an average of about 22 BMPH functional groups was conjugated with about 11 WYRGRLGC (SEQ ID NO: 81) peptides and about 11 GAHWQFNALTVRGGGC (SEQ ID NO: 82) peptides. The mixture containing both peptides was reacted for 2 hours at room temperature followed by purification in ultrapure water and lyophilization.

All intermediates were purified by size-exclusion chromatography using an ÄKTA Purifier FPLC (GE Healthcare) and a column packed with polyacrylamide beads (Bio-Rad Labs). The final product was similarly purified using a column packed with sephadex G-25 beads. After synthesis, the synthetic peptidoglycan can be lyophilized and stored for extended periods of time at −80° C.

Example 2

Lubricin Mimetic

The ability of the lubrican mimetic peptidoglycan to reduce the frictional force between cartilage surfaces was tested as follows. A cartilage plug was glued to the plate of a rheometer, and a second cartilage plug was glued to the rotating fixture of the rheometer. The two cartilage surfaces were put together with a 5N force, and then a shear was applied. The torque was measured and used to calculate the frictional force between the surfaces.

Rheometer

1. Set the conditioning step:
   a. Temperature: 37° C.
   b. Normal Force: 5 N
   c. Normal Force Tolerance: 0.1 N
   d. Duration: 1 hr 2. Set the peak hold steps:
   a. Angular Velocity range: 0.001-100.0 rad/s
   b. Sample Points: 180
   c. Temperature: 37° C.
   d. Duration: 1 hr
   e. Gap limit down: 10000 μm
   f. Gap limit up: 100 μm
3. Weigh the cartilage plugs.
4. Glue the larger cartilage plug to a strip of tape placed inside a large petri dish. Place the petri dish on the rheometer plate and hold it in place with two clamps.
5. Glue the smaller cartilage plug to a strip of tape and place it on the geometry head (20 mm).
6. Add 10 μL of hyaluronic acid to the larger plug and lower the geometry head until both plugs are touching. Add 20 mL of HBSS to the petri dish to maintain hydration.
7. Run the steps and name the file when prompted.
8. Check once in a while if the HBSS has evaporated. If it has, add more.
9. Once the steps are done, open Data Analysis and open the file.
10. Right click on the file name and select Table. A table with the sample points will show up. For the different steps for each sample, a pull down tab appears and you can select one step at a time and the values will show up on the screen.
11. Copy and paste in Excel.
12. Calculate the time in minutes and the torque in N/m.
13. Calculate the total frictional force (F):

$$F = \frac{(3+\alpha)(r_o^3 - r_i^3)}{(2+\alpha)(r_o^4 - r_i^4)} M,$$

where α=1, M=torque, $r_o$=outside radius of plug, and $r_i$=inside radius of plug.

14. Calculate the average frictional force per unit area (f) of the cartilage plugs:

$$f = \frac{F}{\pi(r_o^2 - r_i^2)},$$

where $r_o$=outside radius of plug, $r_i$=inside radius of plug, and F=total frictional force.

15. Calculate the friction coefficient using: μ=F/W where F=total frictional force and W=weight.

Data

Figure 2:
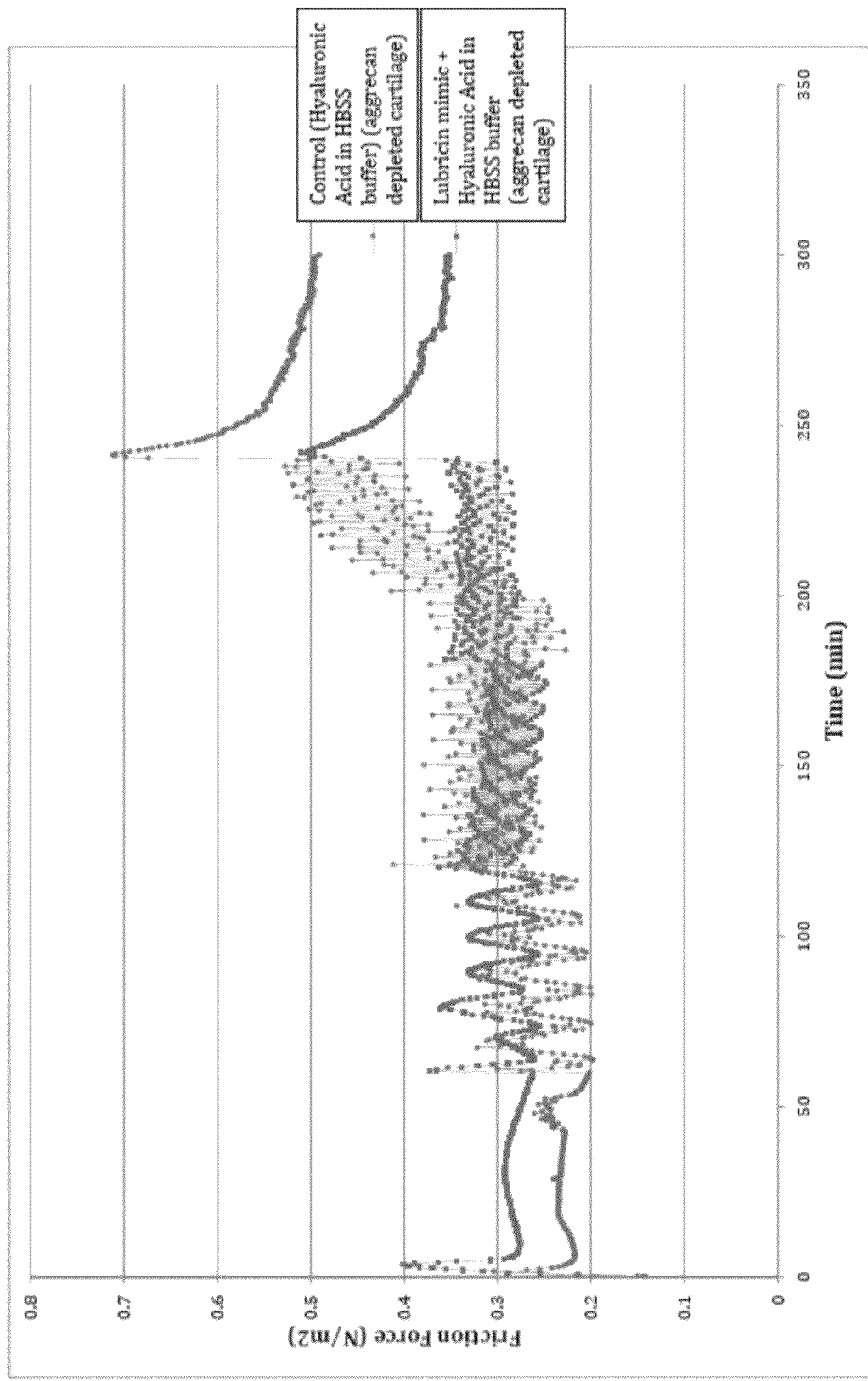
FIG. 2 shows the frictional force in the case of damaged cartilage (with aggrecan depletion to simulate osteoarthritis) and shows that when the synthetic peptidoglycan according to Example 1 is added to the cartilage, friction is lowered between the cartilage surfaces.

FIG. 1 shows the frictional force in the case of undamaged cartilage (with no aggrecan depletion) and shows that with the lubricin mimetic peptidoglycan according to the disclosure, the friction increases between the cartilage surfaces. FIG. 2 shows the frictional force in the case of damaged cartilage (with aggrecan depletion to simulate osteoarthritis) and shows that when the lubricin mimetic peptidoglycan according to the disclosure is added to the cartilage, friction is lowered between the cartilage surfaces. Accordingly, when the lubrican mimetic synthetic peptidoglycan according to the disclosure was applied between the two cartilage surfaces, the frictional force was decreased at higher oscillatory shear, suggesting that it can protect the cartilage during rapid movements.

Example 3

Vitreous Humor Mimetic

Methods

The synthetic peptidoglycans according to the present disclosure can be tested as follows. Viscoelastic properties can be measured using a rheometer, for example the TAInstruments ARG2 rheometer. A cone and plate geometry or a parallel plate geometry can be used. Vitreous humor (e.g., bovine) can be placed within the geometry. The temperature can be controlled and frequency sweeps can be performed from ranges of about 0.1 Hz to about 100 Hz (e.g., 1 Hz) and storage, loss, and complex modulus can be measured at an oscillatory shear stress between about 0.1 Pa and about 10 Pa (e.g., 10 Pa). Temperature: 37° C.

Data

Figure 3:
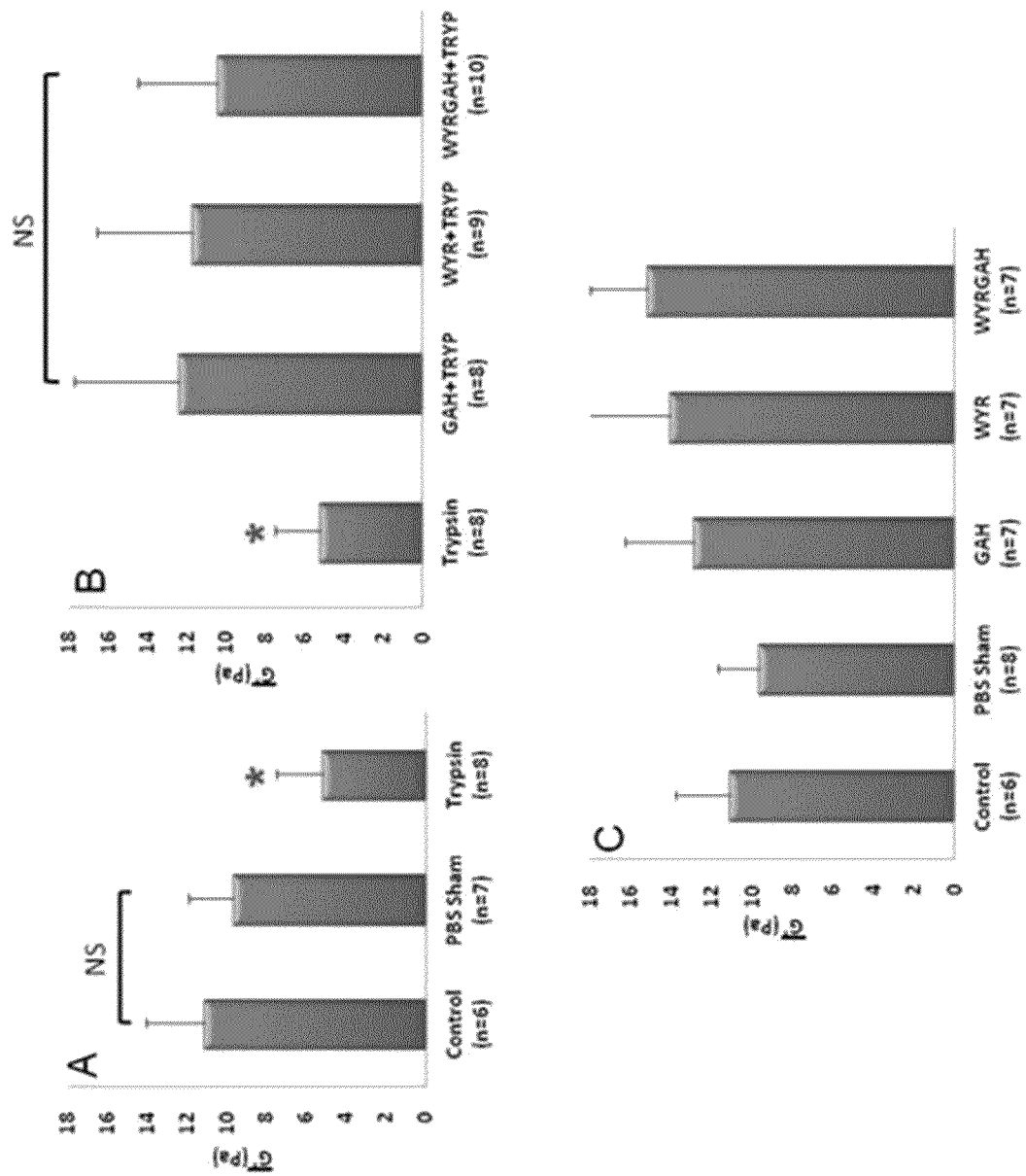
FIG. 3 shows the rheological measurements on bovine vitreous with no treatment (control), PBS buffer and trypsin (FIG. 3A), the rheological measurements on bovine vitreous treated with trypsin, and trypsin in combination with three different peptidoglycans (FIG. 3B), and the rheological measurements on bovine vitreous with no treatment (control), PBS buffer, and three different peptidoglycans without trypsin (FIG. 3C).

FIG. 3A shows the rheological measurements on bovine vitreous with no treatment (control), PBS buffer and trypsin, where the trypsin treated bovine vitreous exhibited a lower viscosity, thus mimicking the disease state.

In FIG. 3B and FIG. 3C, GAH is a synthetic peptidoglycan comprising chondroitin sulfate with hyaluronic acid binding peptide (i.e., GAHWQFNALTVRGGGC (SEQ ID NO: 82)) covalently bonded thereto (via BMPH), WYR is a synthetic peptidoglycan comprising chondroitin sulfate with collagen II binding peptide (i.e., WYRGRLGC (SEQ ID NO: 81)) covalently bonded thereto (via BMPH), and WYRGAH is a mixture of the two synthetic peptidoglycans WYR and GAH just described.

FIG. 3B shows the restoration of the vitreous humor mechanical strength after treatment with the synthetic peptidoglycans.

FIG. 3C shows that the mechanical strength of the vitreous humor is sufficiently maintained in the presence of the synthetic peptidoglycans.

Based on the data shown in FIGS. 3A, 3B and 3C, it is contemplated that the present synthetic peptidoglycans can be used to treat diseases and disorders affecting the vitreous humor.

What is claimed is:

1. An extracellular matrix-binding synthetic peptidoglycan comprising:
   a) a glycan;
   b) from about 1 to about 80 collagen binding peptide(s); and
   c) from about 1 to about 80 hyaluronic acid binding peptide(s);
   wherein the peptides of b) and c) are covalently bonded to the glycan.

2. The synthetic peptidoglycan of claim 1, wherein the glycan is dextran, chondroitin, chondroitin sulfate, dermatan, dermatan sulfate, heparan, heparin, keratin, keratan sulfate, or hyaluronic acid.

3. The synthetic peptidoglycan of claim 1, wherein the glycan is dermatan sulfate.

4. The synthetic peptidoglycan of claim 1, wherein the glycan is chondroitin sulfate.

5. The synthetic peptidoglycan of claim 1, wherein the glycan is hyaluronic acid.

6. The synthetic peptidoglycan of claim 1, wherein the peptides are covalently bonded to the glycan via a linker.

7. The synthetic peptidoglycan of claim 6, wherein the linker is N-[β-maleimidopropionic acid]hydrazide (BMPH).

8. The synthetic peptidoglycan of claim 1, wherein the synthetic peptidoglycan comprises a total of less than about 50 peptides.

9. The synthetic peptidoglycan of claim 1, wherein the synthetic peptidoglycan comprises a total of from about 10 to about 40 peptides.

10. The synthetic peptidoglycan of claim 1, wherein the synthetic peptidoglycan comprises a total of about 22 peptides.

11. The synthetic peptidoglycan of claim 1, wherein the collagen binding peptide has binding affinity to one or more of collagen types I, II, III, or IV.

12. The synthetic peptidoglycan of claim 1, wherein the collagen binding peptide comprises at least one collagen binding peptide that binds to type I collagen and at least one collagen binding peptide that binds to type II collagen.

13. The synthetic peptidoglycan of claim 1, wherein the collagen binding peptide comprises an amino acid sequence selected from the group consisting of:
   i) WYRGRLGC (SEQ ID NO: 81), RRANAALKAGELYKSILYGC (SEQ ID NO: 68), RLDGNEIKRGC (SEQ ID NO: 69), AHEEISTTNEGVMGC (SEQ ID NO: 70), GCGGELYKSILY (SEQ ID NO: 71), NGVFKYRPRYFLYKHAYFYPPLKRFPVQGC (SEQ ID NO: 72), CQDSETRTFY (SEQ ID NO: 60), TKKTLRTGC (SEQ ID NO: 74), GLRSKSKKFRRPDIQYPDATDEDITSHMGC (SEQ ID NO: 75), SQNPVQPGC (SEQ ID NO: 76), SYIRIADTNITGC (SEQ ID NO: 77), SYIRIADTNIT (SEQ ID NO: 64), KELNLVYT (SEQ ID NO: 65), KELNLVYTGC (SEQ ID NO: 78), GSITTIDVPWNV (SEQ ID NO: 67), GELYKSILYGC (SEQ ID NO: 80) and GSITTIDVPWNVGC (SEQ ID NO: 66), or
   ii) any peptide sequence comprising a sequence with at least about 80% sequence identity to the amino acid sequence of i).

14. The synthetic peptidoglycan of claim 1, wherein the collagen binding peptide is WYRGRLGC (SEQ ID NO: 81), RRANAALKAGELYKSILYGC (SEQ ID NO: 68), RLDGNEIKRGC (SEQ ID NO: 69), AHEEISTTNEGVMGC (SEQ ID NO: 70), GCGGELYKSILY (SEQ ID NO: 71), NGVFKYRPRYFLYKHAYFYPPLKRFPVQGC (SEQ ID NO: 72), CQDSETRTFY (SEQ ID NO: 60), TKKTLRTGC (SEQ ID NO: 74), GLRSKSKKFRRPDIQYPDATDEDITSHMGC (SEQ ID NO: 75), SQNPVQPGC (SEQ ID NO: 76), SYIRIADTNITGC (SEQ ID NO: 77), SYIRIADTNIT (SEQ ID NO: 64), KELNLVYT (SEQ ID NO: 65), KELNLVYTGC (SEQ ID NO: 78), GSITTIDVPWNV (SEQ ID NO: 67), GELYKSILYGC (SEQ ID NO: 80) or GSITTIDVPWNVGC (SEQ ID NO: 66).

15. The synthetic peptidoglycan of claim 1, wherein the collagen binding peptide is WYRGRLGC (SEQ ID NO: 81), or a peptide sequence comprising a sequence with at least about 80% sequence identity to SEQ ID NO: 81.

16. The synthetic peptidoglycan of claim 1, wherein the hyaluronic acid binding peptide comprises an amino acid sequence selected from the group consisting of:
   i) GAHWQFNALTVRGG (SEQ ID NO: 2), GDRRRRRMWHRQ (SEQ ID NO: 3), GKHLGGKHRRSR (SEQ ID NO: 4), RGTHHAQKRRS (SEQ ID NO: 5), RRHKSGHIQGSK (SEQ ID NO: 6), SRMHGRVRGRHE (SEQ ID NO: 7), RRRAGLTAGRPR (SEQ ID NO: 8), RYGGHRTSRKWV (SEQ ID NO: 9), RSARYGHRRGVG (SEQ ID NO: 10), GLRGNRRVFARP (SEQ ID NO: 11), SRGQRGRLGKTR (SEQ ID NO: 12), DRRGRSSLPKLAGPVEFPDRKIKGRR (SEQ ID NO: 13), RMRRKGRVKHWG (SEQ ID NO: 14), RGGARGRHKTGR (SEQ ID NO: 15), TGARQRGLQGGWGPRHLRGKDQPPGR (SEQ ID NO: 16), RQRRRDLTRVEG (SEQ ID NO: 17), STKDHNRGRRNVGPVSRSTLRDPIRR (SEQ ID NO: 18), RRIGHQVGGRRN (SEQ ID NO: 19), RLESRAAGQRRA (SEQ ID NO: 20), GGPRRHLGRRGH (SEQ ID NO: 21), VSKRGHRRTAHE (SEQ ID NO: 22), RGTRSGSTR (SEQ ID NO: 23), RRRKKIQGRSKR (SEQ ID NO: 24), RKSYGKYQGR (SEQ ID NO: 25), KNGRYSISR (SEQ ID NO: 26), RRRCGQKKK (SEQ ID NO: 27), KQKIKHVVKLK (SEQ ID NO: 28), KLKSQLVKRK (SEQ ID NO: 29), RYPISRPRKR (SEQ ID NO: 30), KVGKSPPVR (SEQ ID NO: 31), KTFGKMKPR (SEQ ID NO: 32), RIKWSRVSK (SEQ ID NO: 33) and KRTMRPTRR (SEQ ID NO: 34); or ii) any peptide sequence comprising a sequence with at least about 80% sequence identity to the amino acid sequence of i).

17. The synthetic peptidoglycan of claim 1, wherein the hyaluronic acid binding peptide is GAHWQFNALTVRGG (SEQ ID NO: 2), GDRRRRRMWHRQ (SEQ ID NO: 3), GKHLGGKHRRSR (SEQ ID NO: 4), RGTHHAQKRRS (SEQ ID NO: 5), RRHKSGHIQGSK (SEQ ID NO: 6), SRMHGRVRGRHE (SEQ ID NO: 7), RRRAGLTAGRPR (SEQ ID NO: 8), RYGGHRTSRKWV (SEQ ID NO: 9), RSARYGHRRGVG (SEQ ID NO: 10), GLRGNRRVFARP (SEQ ID NO: 11), SRGQRGRLGKTR (SEQ ID NO: 12), DRRGRSSLPKLAGPVEFPDRKIKGRR (SEQ ID NO: 13), RMRRKGRVKHWG (SEQ ID NO: 14), RGGARGRHKTGR (SEQ ID NO: 15), TGARQRGLQGGWGPRHLRGKDQPPGR (SEQ ID NO: 16), RQRRRDLTRVEG (SEQ ID NO: 17), STKDHNRGRRNVGPVSRSTLRDPIRR (SEQ ID NO: 18), RRIGHQVGGRRN (SEQ ID NO: 19), RLESRAAGQRRA (SEQ ID NO: 20), GGPRRHLGRRGH (SEQ ID NO: 21), VSKRGHRRTAHE (SEQ ID NO: 22), RGTRSGSTR (SEQ ID NO: 23), RRRKKIQGRSKR (SEQ ID NO: 24), RKSYGKYQGR (SEQ ID NO: 25), KNGRYSISR (SEQ ID NO: 26), RRRCGQKKK (SEQ ID NO: 27), KQKIKHVVKLK (SEQ ID NO: 28), KLKSQLVKRK (SEQ ID NO: 29), RYPISRPRKR (SEQ ID NO: 30), KVGKSPPVR (SEQ ID NO: 31), KTFGKMKPR (SEQ ID NO: 32), RIKWSRVSK (SEQ ID NO: 33) or KRTMRPTRR (SEQ ID NO: 34).

18. The synthetic peptidoglycan of claim 1, wherein the hyaluronic acid binding peptide is GAHWQFNALTVRGG (SEQ ID NO: 2), or a peptide sequence comprising a sequence with at least about 80% sequence identity to SEQ ID NO: 2.

19. An extracellular matrix-binding synthetic peptidoglycan comprising:
    a) chondroitin sulfate;
    b) from about 1 to about 80 collagen binding peptide(s); and
    c) from about 1 to about 80 hyaluronic acid binding peptide(s);
    wherein the peptides of b) and c) are covalently bonded to the glycan; and further wherein the collagen binding peptide(s) is WYRGRLGC (SEQ ID NO: 81), or a peptide sequence comprising a sequence with at least about 80% sequence identity to SEQ ID NO: 81, and the hyaluronic acid binding peptide(s) is GAHWQFNALTVRGG (SEQ ID NO: 2), or a peptide sequence comprising a sequence with at least about 80% sequence identity to SEQ ID NO: 2.

20. The synthetic peptidoglycan of claim 19, wherein the peptides are covalently bonded to the glycan via a linker.

21. The synthetic peptidoglycan of claim 20, wherein the linker is N-[β-maleimidopropionic acid]hydrazide (BMPH).

22. An extracellular matrix-binding synthetic peptidoglycan comprising:
    a) chondroitin sulfate;
    b) from about 5 to about 20 collagen binding peptide(s); and
    c) from about 5 to about 20 hyaluronic acid binding peptide(s);
    wherein the peptides of b) and c) are covalently bonded to the glycan via N-[β-maleimidopropionic acid]hydrazide (BMPH); and further wherein the collagen binding peptide(s) are WYRGRLGC (SEQ ID NO: 81), or a peptide sequence comprising a sequence with at least about 80% sequence identity to SEQ ID NO: 81, and the hyaluronic acid binding peptide(s) are GAHWQFNALTVRGG (SEQ ID NO: 2), or a peptide sequence comprising a sequence with at least about 80% sequence identity to SEQ ID NO: 2.

23. A pharmaceutical composition comprising the extracellular matrix-binding synthetic peptidoglycan of claim 1.

24. A method of treating and/or preventing degradation of a hyaluronic acid rich tissue in a patient comprising administering to a patient in need thereof the pharmaceutical composition of claim 23.

25. The method of claim 24, wherein the hyaluronic acid rich tissue is the skin.

26. A method of treating and/or preventing cartilage degeneration in a patient comprising administering to a patient in need thereof the pharmaceutical composition of claim 23.

27. A method of treating and/or preventing cartilage degeneration in a patient comprising injecting the pharmaceutical composition of claim 23 into a synovial cavity of a patient in need thereof.

28. A method of treating and/or preventing vitreous humor degeneration in a patient comprising administering to a patient in need thereof the pharmaceutical composition of claim 23.

29. A method of treating and/or preventing nucleus pulposus degeneration in a patient comprising administering to a patient in need thereof the pharmaceutical composition of claim 23.

* * * * *

SEQUENCE LISTING

<160> NUMBER OF SEQ ID NOS: 84

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

-continued

Gly Ala His Trp Gln Phe Asn Ala Leu Thr Val Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala His Trp Gln Phe Asn Ala Leu Thr Val Arg Gly Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Asp Arg Arg Arg Arg Arg Met Trp His Arg Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Lys His Leu Gly Gly Lys His Arg Arg Ser Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Thr His His Ala Gln Lys Arg Arg Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg His Lys Ser Gly His Ile Gln Gly Ser Lys
1               5                   10

<210> SEQ ID NO 7
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 7

Ser Arg Met His Gly Arg Val Arg Gly Arg His Glu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Arg Ala Gly Leu Thr Ala Gly Arg Pro Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Tyr Gly Gly His Arg Thr Ser Arg Lys Trp Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ala Arg Tyr Gly His Arg Arg Gly Val Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Leu Arg Gly Asn Arg Arg Val Phe Ala Arg Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Arg Gly Gln Arg Gly Arg Leu Gly Lys Thr Arg
1               5                   10
```

```
<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg Arg Gly Arg Ser Ser Leu Pro Lys Leu Ala Gly Pro Val Glu
1               5                   10                  15

Phe Pro Asp Arg Lys Ile Lys Gly Arg Arg
            20                  25

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Met Arg Arg Lys Gly Arg Val Lys His Trp Gly
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Gly Ala Arg Gly Arg His Lys Thr Gly Arg
1               5                   10

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Gly Ala Arg Gln Arg Gly Leu Gln Gly Gly Trp Gly Pro Arg His
1               5                   10                  15

Leu Arg Gly Lys Asp Gln Pro Pro Gly Arg
            20                  25

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Gln Arg Arg Arg Asp Leu Thr Arg Val Glu Gly
1               5                   10

<210> SEQ ID NO 18
<211> LENGTH: 26
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 18

Ser Thr Lys Asp His Asn Arg Gly Arg Arg Asn Val Gly Pro Val Ser
1               5                   10                  15

Arg Ser Thr Leu Arg Asp Pro Ile Arg Arg
            20                  25

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Ile Gly His Gln Val Gly Gly Arg Arg Asn
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Leu Glu Ser Arg Ala Ala Gly Gln Arg Arg Ala
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Pro Arg Arg His Leu Gly Arg Arg Gly His
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Ser Lys Arg Gly His Arg Arg Thr Ala His Glu
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

Arg Gly Thr Arg Ser Gly Ser Thr Arg
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Arg Lys Lys Ile Gln Gly Arg Ser Lys Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Lys Ser Tyr Gly Lys Tyr Gln Gly Arg
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Asn Gly Arg Tyr Ser Ile Ser Arg
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Arg Cys Gly Gln Lys Lys Lys
1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Gln Lys Ile Lys His Val Val Lys Leu Lys
1               5                   10

<210> SEQ ID NO 29
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 29

Lys Leu Lys Ser Gln Leu Val Lys Arg Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Tyr Pro Ile Ser Arg Pro Arg Lys Arg
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Val Gly Lys Ser Pro Pro Val Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Thr Phe Gly Lys Met Lys Pro Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ile Lys Trp Ser Arg Val Ser Lys
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Arg Thr Met Arg Pro Thr Arg Arg
1               5
```

```
<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Arg Ala Ser Arg Ser Arg Gly Gln Val Gly Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Gly Thr His His Ala Gln Lys Arg Arg Ser
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Pro Val Arg Arg Leu Gly Thr Pro Val Val Gly
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Arg Arg Ala Glu Gly Lys Thr Arg Met Leu Gln
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Lys Val Arg Gly Arg Arg His Gln Ala Ser Gly
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 40

Ser Asp Arg His Arg Arg Arg Glu Ala Asp Gly
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Gln Arg Val Arg Arg Val Lys His Pro Pro Gly
1               5                   10

<210> SEQ ID NO 42
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Glu Arg Arg Glu Arg His Ala Val Ala Arg His Gly Pro Gly Leu
1               5                   10                  15

Glu Arg Asp Ala Arg Asn Leu Ala Arg Arg
            20                  25

<210> SEQ ID NO 43
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Val Arg Pro Gly Gly Lys Arg Gly Gly Gln Val Gly Pro Pro Ala
1               5                   10                  15

Gly Val Leu His Gly Arg Arg Ala Arg Ser
            20                  25

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Val Arg Ser Arg Arg Gly His Arg Met Asn Ser
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Arg Arg Arg Gly Arg Thr Arg Asn Ile Gly Asn
```

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Lys Thr Ala Gly His Gly Arg Arg Trp Ser Arg Asn
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Ala Lys Arg Gly Glu Gly Arg Arg Glu Trp Pro Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Gly Gly Asp Arg Arg Lys Ala His Lys Leu Gln Ala
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Arg Arg Gly Gly Arg Lys Trp Gly Ser Phe Glu Gly
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Arg Gln Arg Arg Arg Asp Leu Thr Arg Val Glu Gly
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic

```
                                  peptide

<400> SEQUENCE: 51

Arg Asp Gly Thr Arg Tyr Val Gln Lys Gly Glu Tyr Arg
1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Arg Glu Ala Arg Ser Gly Lys Tyr Lys
1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Asp Lys Lys His Lys Leu Tyr Gly Val
1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Asp Lys Glu Arg Ser Arg Tyr Asp Val
1               5                  10

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Arg Ala Asn Ala Ala Leu Lys Ala Gly Glu Leu Tyr Lys Ser Ile
1               5                  10                  15

Leu Tyr

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Leu Asp Gly Asn Glu Ile Lys Arg
1               5
```

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala His Glu Glu Ile Ser Thr Thr Asn Glu Gly Val Met
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Glu Leu Tyr Lys Ser Ile Leu Tyr
1               5

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln
            20                  25

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Gln Asp Ser Glu Thr Arg Thr Phe Tyr
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Lys Lys Thr Leu Arg Thr
1               5

<210> SEQ ID NO 62
<211> LENGTH: 28
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 62

Gly Leu Arg Ser Lys Ser Lys Phe Arg Arg Pro Asp Ile Gln Tyr
1               5                   10                  15

Pro Asp Ala Thr Asp Glu Asp Ile Thr Ser His Met
            20                  25

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Gln Asn Pro Val Gln Pro
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Tyr Ile Arg Ile Ala Asp Thr Asn Ile Thr
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Glu Leu Asn Leu Val Tyr Thr
1               5

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ser Ile Thr Thr Ile Asp Val Pro Trp Asn Val Gly Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Ile Thr Thr Ile Asp Val Pro Trp Asn Val

```
<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Arg Ala Asn Ala Ala Leu Lys Ala Gly Glu Leu Tyr Lys Ser Ile
1               5                   10                  15

Leu Tyr Gly Cys
            20

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Leu Asp Gly Asn Glu Ile Lys Arg Gly Cys
1               5                   10

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala His Glu Glu Ile Ser Thr Thr Asn Glu Gly Val Met Gly Cys
1               5                   10                  15

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Cys Gly Gly Glu Leu Tyr Lys Ser Ile Leu Tyr
1               5                   10

<210> SEQ ID NO 72
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln Gly Cys
            20                  25                  30
```

```
<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Gln Asp Ser Glu Thr Arg Thr Phe Tyr Gly Cys
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Lys Lys Thr Leu Arg Thr Gly Cys
1               5

<210> SEQ ID NO 75
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met Gly Cys
            20                  25                  30

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Gln Asn Pro Val Gln Pro Gly Cys
1               5

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Tyr Ile Arg Ile Ala Asp Thr Asn Ile Thr Gly Cys
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 78

Lys Glu Leu Asn Leu Val Tyr Thr Gly Cys
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Cys Gly Gly Glu Leu Tyr Lys Ser Ile Leu Tyr Gly Cys
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Glu Leu Tyr Lys Ser Ile Leu Tyr Gly Cys
1               5                   10

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Tyr Arg Gly Arg Leu Gly Cys
1               5

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ala His Trp Gln Phe Asn Ala Leu Thr Val Arg Gly Gly Gly Cys
1               5                   10                  15

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gly Gly Cys
1

<210> SEQ ID NO 84
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ser Gly Cys
1
```